(12) United States Patent
Brady

(10) Patent No.: US 9,658,155 B2
(45) Date of Patent: May 23, 2017

(54) SYSTEM AND METHOD FOR IDENTIFYING MATERIALS USING A THZ SPECTRAL FINGERPRINT IN A MEDIA WITH HIGH WATER CONTENT

(71) Applicant: Patrick K Brady, Glen Ellyn, IL (US)

(72) Inventor: Patrick K Brady, Glen Ellyn, IL (US)

(*) Notice: Subject to any disclaimer, the term of this patent is extended or adjusted under 35 U.S.C. 154(b) by 575 days.

(21) Appl. No.: 14/108,138

(22) Filed: Dec. 16, 2013

(65) Prior Publication Data

US 2014/0172374 A1 Jun. 19, 2014

Related U.S. Application Data

(60) Provisional application No. 61/738,199, filed on Dec. 17, 2012.

(51) Int. Cl.
*H03F 1/26* (2006.01)
*H04B 15/00* (2006.01)
*G01N 21/3581* (2014.01)

(52) U.S. Cl.
CPC .............................. *G01N 21/3581* (2013.01)

(58) Field of Classification Search
CPC ........... G01N 21/3581; G01N 33/4972; G01N 21/3504; G01N 21/272; C12Q 2537/143; C12Q 2525/15; C12Q 1/6809; C12Q 1/6853; C12Q 1/54; C12Q 2525/155; C12Q 2525/161; C12Q 1/26; C12Q 1/686; C12Q 1/04; C12Q 1/70
USPC ................................ 702/189; 250/341.8, 349
See application file for complete search history.

(56) References Cited

U.S. PATENT DOCUMENTS

| 2,498,461 | A | 2/1950 | Skellett |
| 4,533,829 | A | 8/1985 | Miceli et al. |
| 4,888,061 | A | 12/1989 | Wenz |
| 5,043,739 | A | 8/1991 | Logan et al. |
| 5,450,053 | A | 9/1995 | Wood |
| 6,534,784 | B2 | 3/2003 | Eliasson et al. |
| 6,617,963 | B1 | 9/2003 | Watters et al. |
| 7,436,373 | B1 | 10/2008 | Lopes et al. |
| 7,652,572 | B2 | 1/2010 | Roybal et al. |

(Continued)

FOREIGN PATENT DOCUMENTS

| WO | 2007070541 | 4/2009 |
| WO | 2012153210 | 11/2012 |

OTHER PUBLICATIONS

Shelton, et al., "Gangbuster frequency selective surface metamaterials in terahertz band," Elctronics Letters, vol. 44, No. 22, pp. 1-2 (Oct. 23, 2008).

(Continued)

*Primary Examiner* — Roy Y Yi
(74) *Attorney, Agent, or Firm* — Fitzgerald & Isaacson, LLP; David C. Isaacson

(57) ABSTRACT

A material detector includes a pulse generator to generate pulses to excite molecules in the material and a detector to detect a signal generated from excited molecules in the terahertz region. Spectral features in the material are analyzed to identify the material. Detection can be performed using a nanoantenna array structure having antennas tuned to detect the expected spectral emission. The nanoantenna array can include antennas having MIM or MIIM diodes. Signal processing and statistical analysis is use to reduce false positives and false negative in identifying the material.

28 Claims, 19 Drawing Sheets

(56) References Cited

U.S. PATENT DOCUMENTS

| | | | |
|---|---|---|---|
| 7,792,644 | B2 | 9/2010 | Kotter et al. |
| 8,071,931 | B2 | 12/2011 | Novack et al. |
| 8,115,683 | B1 | 2/2012 | Stefanakos et al. |
| 8,283,619 | B2 | 10/2012 | Novack et al. |
| 8,847,824 | B2 | 9/2014 | Kotter et al. |
| 8,901,507 | B2 | 12/2014 | Kotter |
| 2003/0128919 | A1 | 7/2003 | Weiss et al. |
| 2006/0111619 | A1 | 5/2006 | Castiglione et al. |
| 2006/0210279 | A1 | 9/2006 | Hillis et al. |
| 2006/0283539 | A1 | 12/2006 | Slafer |
| 2007/0158571 | A1 | 7/2007 | Cole et al. |
| 2007/0198222 | A1* | 8/2007 | Schuster ............... G01D 1/00 702/187 |
| 2008/0060455 | A1 | 3/2008 | Coyle |
| 2008/0156991 | A1 | 7/2008 | Hu et al. |
| 2008/0170218 | A1 | 7/2008 | Dantus et al. |
| 2008/0231443 | A1 | 9/2008 | Kotter et al. |
| 2009/0125254 | A1 | 5/2009 | Kotter et al. |
| 2009/0212217 | A1 | 8/2009 | Mann et al. |
| 2009/0272906 | A1 | 11/2009 | Gratton |
| 2009/0323754 | A1* | 12/2009 | Branly .................. H01S 3/092 372/70 |
| 2010/0044570 | A1 | 2/2010 | McGill et al. |
| 2010/0067844 | A1 | 3/2010 | Sanders |
| 2010/0270967 | A1 | 10/2010 | Cho et al. |
| 2010/0284086 | A1 | 11/2010 | Novack et al. |
| 2010/0319749 | A1 | 12/2010 | Greiff et al. |
| 2011/0062329 | A1 | 3/2011 | Ben-Bassat |
| 2011/0122407 | A1* | 5/2011 | Jalali ..................... G01N 21/65 356/301 |
| 2011/0277805 | A1* | 11/2011 | Novack .................. H01Q 1/248 136/243 |
| 2011/0315880 | A1 | 12/2011 | Nemirovsky |
| 2012/0080073 | A1 | 4/2012 | Kotter et al. |
| 2012/0153168 | A1 | 6/2012 | Langeveld |
| 2012/0175521 | A1 | 7/2012 | Chawla et al. |
| 2012/0224167 | A1 | 9/2012 | Sanders et al. |
| 2012/0305773 | A1 | 12/2012 | Wu et al. |
| 2013/0009851 | A1 | 1/2013 | Danesh |
| 2013/0146117 | A1 | 6/2013 | Brady |
| 2013/0249771 | A1* | 9/2013 | Kotter .................... H01Q 1/248 343/893 |
| 2015/0303335 | A1 | 10/2015 | Kotter |

OTHER PUBLICATIONS

Kotter et al., "Lithographic Antennas for Enhancement of Solar-Cell Efficiency," Idaho Nat'l Eng'g. Lab., INEE/EXT-98-00389, Apr. 1998, 26 pages.

Kotter et al., "Theory and manufacturing processes of solar nanoantenna electromagnetic collectors," Journal or Solar Energy Engineering, ASME International US, vol. 132, No. 1, Feb. 1, 2010 (Feb. 1, 2010), pp. 11014-1-11014-9.

Notification of Transmittal of International Search Report and Written Opinion of International Searching Authority mailed Aug. 15, 2014 in PCT App. No. PCT/US2014/017843, filed Feb. 21, 2014.

International Search Report mailed Aug. 15, 2014 in PCT App. No. PCT/US2014/017843, filed Feb. 21, 2014.

Written Opinion of the International Searching Authority mailed Aug. 15, 2014 in PCT App. No. PCT/US2014/017843, filed Feb. 21, 2014.

Notification of Transmittal of International Search Report and Written Opinion of International Searching Authority, or the Declaration mailed Sep. 4, 2015 in PCT App. No. PCT/US2015/036817, filed Jun. 19, 2015.

International Search Report mailed Sep. 4, 2015 in PCT App. No. PCT/US2015/036817, filed Jun. 19, 2015.

Written Opinion of the International Searching Authority mailed Sep. 4, 2015 in PCT App. No. PCT/US2015/036817, filed Jun. 19, 2015.

Remski et al., "Frequency Selective Surfaces, Design and Analysis Using the Ansoft Produce Suite," Ansoft Corp., Presentation #4, 34 pages, 2000.

International Search Report for International Application No. PCT/US2013/077561 dated Mar. 27, 2015, 2 pages.

International Written Opinion for International Application No. PCT/US2013/077561 dated Mar. 27, 2015, 2 pages.

U.S. Appl. No. 60/987,630, filed Nov. 13, 2007, titled, "Antenna Devices Comprising Flexible Substrates, Related Structures, and Methods of Making and Using the Same," to Pinhero et al.

Kotter, D., et al., "Theory and Manufacturing Processes of Solar Nanoantenna Electromagnetic Collectors", The Journal of Solar Energy Engineering, Feb. 2010, vol. 132.

Monacelli B., et al., "Infrared frequency selective surface based on circuit-analog square loop design," IEEE Transactions on Antennas and Propagation, vol. 53, No. 2, pp. 745-752, Feb. 2005.

Notification of Transmittal of International Search Report and Written Opinion of International Searching Authority mailed Jun. 13, 2014 in PCT App. No. PCT/US2013/075495, filed Dec. 16, 2013.

International Search Report mailed Jun. 13, 2014 in PCT App. No. PCT/US2013/075495, filed Dec. 16, 2013.

Written Opinion of the International Searching Authority mailed Jun. 13, 2014 in PCT App. No. PCT/US2013/075495, filed Dec. 16, 2013.

Luvkofsky, David, et al., "Can Precursors Improve the Transmission of Energy at Optical Frequencies?," Journal of Modern Optics, vol. 56, No. 9, 1083-90 (May 20, 2009).

Celanovic, I., et al. "Two-dimensional tungsten photonic crystals as selective thermal emitters," Applied Physics Letters 92, pp. 193101-1-3 (2008).

Grischkowsky, D., et al., "Far-infrared time-domain spectroscopy with terahertz beams of dielectrics and semiconductors," J. Opt. Soc. Am., vol. 7, No. 10, pp. 2006-2015 (Oct. 1990).

Notification of Transmittal of International Search Report and Written Opinion of International Searching Authority mailed Feb. 15, 2013 in PCT App. No. PCT/US2012/068561, filed Dec. 7, 2012.

International Search Report mailed Feb. 15, 2013 in PCT App. No. PCT/US2012/068561, filed Dec. 7, 2012.

Written Opinion of the International Searching Authority mailed Feb. 15, 2013 in PCT App. No. PCT/US2012/068561, filed Dec. 7, 2012.

* cited by examiner $$\frac{\partial \rho_1}{\partial t} = -\frac{1}{T'_2}\rho_1 + \omega_0 \rho_2,$$

$$\frac{\partial \rho_2}{\partial t} = -\frac{1}{T'_2}\rho_2 - \omega_0 \rho_2 + 2\frac{\mu}{\hbar}E\rho_3,$$

$$\frac{\partial \rho_2}{\partial t} = -\frac{1}{T'_2}(\rho_3 - \rho_{30}) - 2\frac{\mu}{\hbar}E\rho_2,$$

FIG. 5

SYSTEM AND METHOD FOR IDENTIFYING MATERIALS USING A THZ SPECTRAL FINGERPRINT IN A MEDIA WITH HIGH WATER CONTENT

This application claims the benefit of U.S. Provisional Patent App. No. 61/738,199, filed Dec. 17, 2012, which is hereby incorporated by reference in its entirety.

BACKGROUND

Field of the Invention

Embodiments of the present invention relate generally to structures and methods for detecting materials, including explosives or contraband, using a terahertz (THz) fingerprint.

Background of the Invention

Explosive materials exhibit a distinct THz fingerprint in the terahertz (THz) frequency range that offers a unique characteristic for discrimination and detection. Detecting this signature would allow for detection of such materials that may be hidden in luggage, the body or elsewhere. In addition, THz imaging offers the promise of a nonintrusive technique to detect contraband hidden on the human body.

However, current THz spectrometer systems have limited performance in a stand-alone detection mode of operation. Moreover, they are not able to penetrate high water content media, such as the human body. Even frequencies in the near infrared (NIR) band do not provide a solution because skin and outer layer materials (e.g., clothing) are likely to be opaque to infrared radiation.

Conventional THz detection systems rely on broad-band detectors to detect THz radiation. Typically, they require mechanically tunable interferometers to achieve spectral resolution. To achieve the required sensitivity, conventional THz detectors also require cooling to liquid helium temperatures. While THz spectrometer systems exist, they are too bulky and fragile for field applications.

Thus, there is a need to provide data analysis methods and detection/discrimination processes to identify and classify threats and to reduce false alarms.

BRIEF SUMMARY OF THE INVENTION

In an embodiment, a terahertz (THz) detector system implements a femtosecond pulsed THz beam to actively illuminate suspect "targets." The short duration of these pulses and the broadband spectral content exploits the property of coherent bleaching to penetrate to depths through high water content materials. Reflections from change in material boundaries and absorption spectra from non-biological material are detected by THz antenna arrays tuned to the known absorption frequencies of the material of interest, such as explosives or other contraband. Spectral signatures or "fingerprints" are matched using these arrays in ensemble. Multiple spectral peak detection combined with application of signal processing algorithms enhances detection to reduce false positives (indicating the presence of a material of interest that is, in fact, not present) and lower false negatives (failing to indicate the presence of a material of interest that is, in fact, present).

In an embodiment, a system to detect a material comprises a pulse generator to generate a terahertz pulse to excite molecules in the material, a detector to detect a signal having spectral components in the terahertz region emitted from the excitations, and a processor to perform statistical analysis and signal processing on the detected signal to reduce false positives and false negatives of detection.

In another embodiment, a method for detecting a material comprises generating a pulse to excite molecules in the material, detecting a signal having spectral components in the terahertz region emitted from the excitations, and performing statistical analysis and signal processing on the detected signal to reduce false positives and false negatives of detection.

In another embodiment, a method for classifying THZ spectral data as representing specific objects comprises simulating security screening scenarios, collecting THz spectral data representative of the objects, extracting features from the magnetic data that distinguish respective objects, and performing a pre-classification optimization method on the features.

Additional features and embodiments of the present invention will be evident in view of the following detailed description of the invention.

BRIEF DESCRIPTION OF THE DRAWINGS

FIG. 5 is a set of coupled Maxwell-Bloch equations that can be used to model a coherent bleaching region of a coherent material according to an embodiment of the present invention.

DETAILED DESCRIPTION

Molecules have unique vibrational and rotational frequencies in the Terahertz (THz) region. These unique spectral features in essence form a fingerprint of the molecules. Pulses in the THz range can be generated and used to excite these spectral features of molecules of a material of interest, such as an explosive or other contraband or material of interest. This fingerprint can be exploited to identify a particular material being surveyed. For example, the explosive material RDX exhibits spectral lines at 0.82, 1.05, 1.96, 2.20, and 3.08 THz. Simultaneous detection of several of these wavelengths in a material of interest being analyzed indicates a likely presence of the RDX material in the material of interest. Statistical analysis and signal processing techniques can be used to reduce false indications (false positives—indicating the presence of a material of interest when it is not present or false negatives—not indicating the presence of a material of interest when it is present). Other materials may be identified in a similar fashion.

Figure 1:
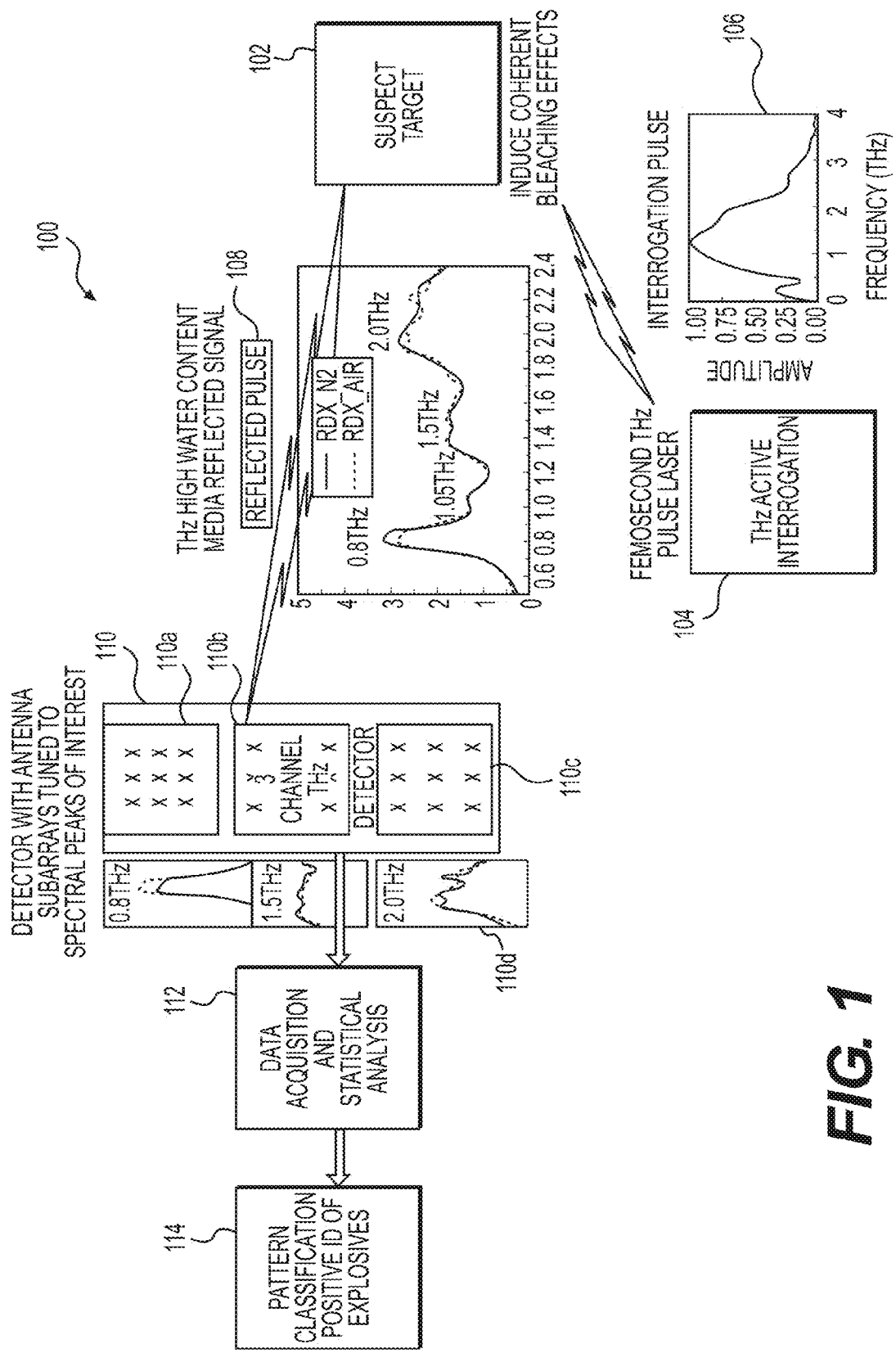
FIG. 1 is a schematic diagram of a system for detecting the presence of a material of interest using THz excitation pulses according to an embodiment of the present invention.

FIG. 1 is a schematic diagram of a system 100 for detecting the presence of a material of interest using THz excitation pulses according to an embodiment of the present invention. In an embodiment a suspect target 102, which may contain a material of interest, is illuminated by an interrogation pulse 106 in the THz frequency range emitted by an interrogation pulse source 104. In an embodiment, interrogation pulse source 104 is a femtosecond THz pulse laser. An exemplary such laser is described in more detail below.

In an embodiment, illumination of suspect target 102 with THz interrogation pulse 106 induces coherent bleaching. Coherent bleaching reduces absorption of the pulse 106 propagating through the material being interrogated. This allows THz interrogation pulse 106 to penetrate to depths in the material being interrogated, particularly organic materials, such as explosives, or material with high water content, such as human tissue.

Illumination of suspect material 102 generates a reflected pulse 108. Reflected pulse 108 is a modified version of THz interrogation pulse 106, which modifications are dependent upon, and indicative of, the molecular composition of suspect target 102. For example, reflected pulse 108 exhibits a spectrum characteristic of molecules comprising suspect target 102. This spectral "fingerprint" can be used to identify materials of interest in suspect target 102, such as explosives or other contraband.

To determine the spectral "fingerprint", reflected pulse 108 is directed to an antenna/diode detector array 110. Antenna/diode detector array 110 comprises a plurality of antennae (and/or diodes or other detection devices) that detect the spectral components of reflected pulse 108. The antennae/diode detectors in antenna/diode array 110 are also referred to as "sensors". As shown in FIG. 1, for example, antenna/diode detector array 110 comprises three antenna/diode detector subarrays 110a, 110b, and 110c. Each antenna/diode detector subarray 110a, 110b, and 110c comprises one or more antennae that are tuned to a particular frequency. Other embodiments are possible. For example, detector antenna/diode arrays may comprise a plurality of antenna/diode subarrays with each antenna/diode subarray tuned to a frequency band. Such an embodiment breaks up the frequency spectrum evenly for a more general purpose device (similar to a mass spectrometer).

The output of antenna/diode detector array 110 is supplied to a data acquisition and statistical analysis module 112. Data acquisition and statistical analysis module 112 processes the output of antenna/diode detector array 110 to determine the spectral content of reflected pulse 108. For example, in an embodiment, data acquisition and statistical analysis module 112 comprises one or more matched filters that are tuned to detect spectral components of interest. For example, as shown in FIG. 1, the spectral components of interest are 0.8 THz, 1.5 THz, and 2.0 THz. Consequently, data acquisition and statistical analysis module 112 would comprise three matched filters: one tuned to detect 0.8 THz, one tuned to detect 1.5 THz, and one tuned to detect 2.0 THz. In embodiments, data acquisition and statistical analysis module 112 may include other processing to better detect the spectral content of antenna/diode detector array output 110, and thereby reduce false positives (indicating the presence of a material of interest that is not present) and false negatives (failing to indicate the presence of a material of interest that is present). The system incorporates a series of detectors that perform single-point absorption peak measurements and matched-filter analysis. It does not require scanning of the full spectrum and FFT post processing of datasets. Each antenna is 'tuned' to a selective bandpass representing a unique spectral absorption peak of the explosive material.

Data analysis extracts unique spectral features, including: frequency of absorption peaks, peak widths, ratio between peak heights and peak slope to serve as discriminators of threat materials. Data acquisition and statistical analysis module 112 provides its output to a pattern classification module 114. Pattern classification module 114 comprises a database of spectral content of the reflected pulse of one or more materials of interest when interrogated by a THz interrogation pulse. Pattern classification module 114 compares the spectral component output from data acquisition and statistical analysis module 112 with the spectral content of one or more of the materials stored in its database. Pattern classification algorithms match spectra to a database of validated spectra. Pattern classification module 114 can provide an alert or warning if there is a match. The alert can be audible, visual, or any other way to provide an alert that a material of interest, such as an explosive or other contraband was detected.

Detection of frequencies in the THz band requires new photonic and electronic devices suited to the THz band. For example, in an embodiment, a femtosecond pulse THz laser drive source is used as THz interrogation source 102. Such a source penetrates high water content materials based on the phenomenon of coherent bleaching that overcomes the limitations of conventional THz detectors.

Further, in an embodiment, antenna/diode detector array 110 comprises Antenna Coupled Diode rectifiers (ACT Detectors or ACT Devices). ACT devices comprise nanoantenna structures combined with resonant tunneling Metal Insulator Metal diodes (MIM). In another embodiment, the nanoantenna structure comprises Metal Insulator Insulator Metal diodes (MIIM). These structures are assembled into antenna arrays, such as antenna/diode detector array 110, and designed for operation at frequencies in the THz band. Not only can such antenna arrays be used to detect materials of interest, but they can be configured for imaging as well. Exemplary nanoantenna structures are described in co-pending U.S. patent application Ser. No. 13/708,481, filed Dec. 7, 2012, entitled, "System and Method for Converting Electromagnetic Radiation to Electrical Energy" to Patrick K. Brady, which is hereby incorporated by reference in its entirety.

Figure 2:
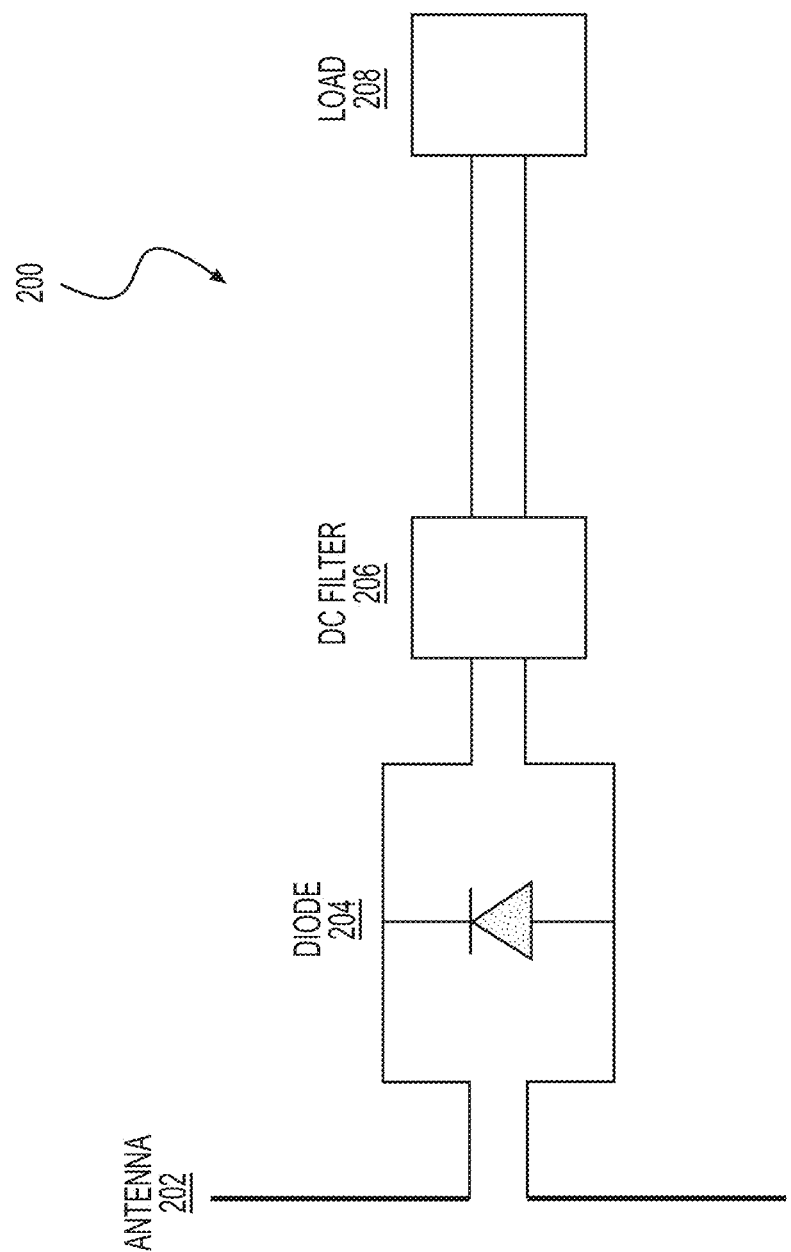
FIG. 2 is a schematic diagram of an exemplary antenna-coupled diode rectifier (ACT device) 200 according to an embodiment.
Figure 3:
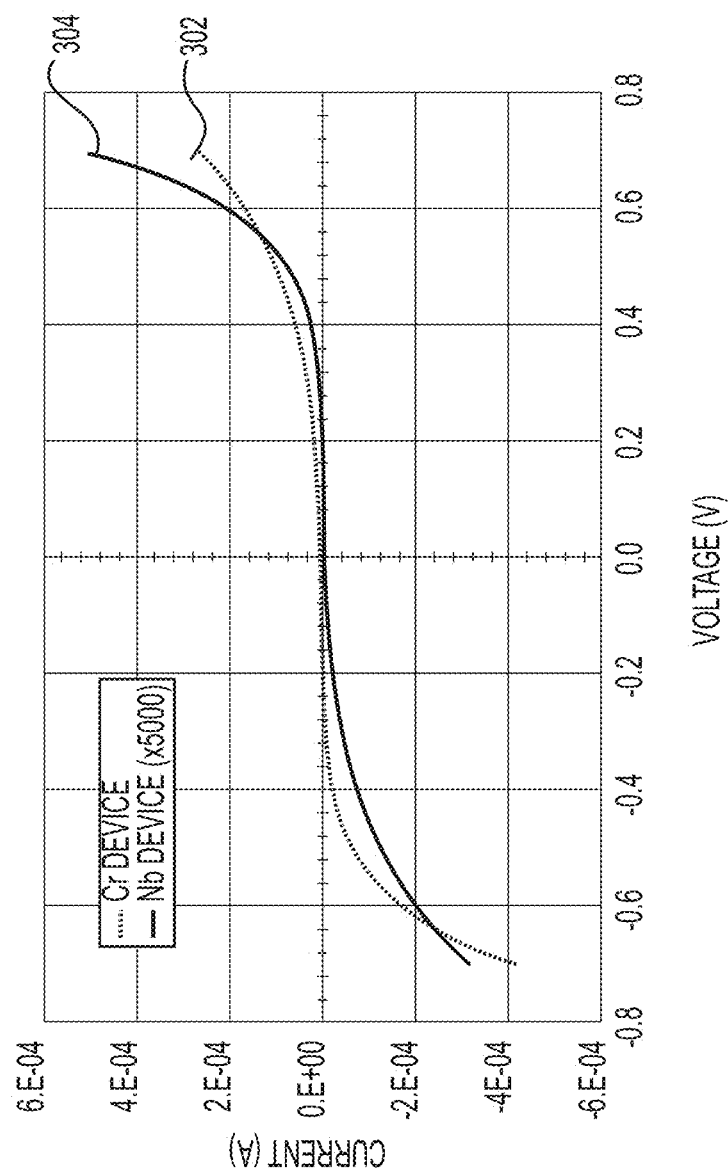
FIG. 3 is a graph that shows the current-voltage (I-V) characteristics for two types of MIMs that can be used according to embodiments of the present invention.

FIG. 2 is a schematic diagram of an exemplary antenna-coupled diode rectifier (ACT device) 200 according to an embodiment. In an embodiment, ACT device 200 comprises an antenna 202, a diode 204, and a DC filter 206. Antenna 202 resonates in the presence of energy to which it is tuned, for example, energy in the THz frequency range, and passes energy to diode 204. Diode 204 converts the energy generated by antenna 202 to direct current (DC). In an embodiment, diode 204 is a MIM diode. In another embodiment, diode 204 is a MIIM diode or other combination of metals and multiple inner insulators. The generated DC current is passed to DC filter 206, which smoothes the generated DC current. ACT device 200 can be coupled to a load 208. Consequently, ACT device 200 delivers current to load 208 when in the presence of radiation to which it is tuned. Various circuits such as analog to digital convertors or digital logic circuits may be substituted for load circuit 208 depending upon the application and data acquisition system. Such circuits would be well known to those skilled in the art. ACT detectors, such as ACT detector 200, are used in a THz spectroscopy system because they exhibit an excellent noise-equivalent power (NEP), a very fast response, and can operate at room temperature. FIG. 3 is a graph that shows the current-voltage (I-V) characteristics for two types of MIMs that can be used in embodiments. Curve 1702 corresponds to a Cr/Cr$_2$O$_3$/Cr MIM diode. Curve 1704 corresponds to a Nb/Nb$_2$O$_5$/Nb MIM diode. Using electron-beam lithography the Cr/Cr$_2$O$_3$/Cr diodes can be fabricated with bowtie or other antennas to form ACT devices to use in embodiments.

Lower impedance MIM diodes, such as those with a NiO insulator and Ni electrodes, may provide an improved impedance match with the antenna (such as antenna 202), due to the lower barrier heights of such materials. However, the improved impedance matching of such a MIM device may come at the cost of reduced responsiveness (DC current out per unit AC power in) that results from the lower diode nonlinearity of low barrier-height devices.

The desire for both low impedance and high responsivity indicates using a double-insulator MIIM diode instead of a single insulator device. The additional insulator layer increases diode nonlinearity without increasing the diode impedance.

Figure 4:
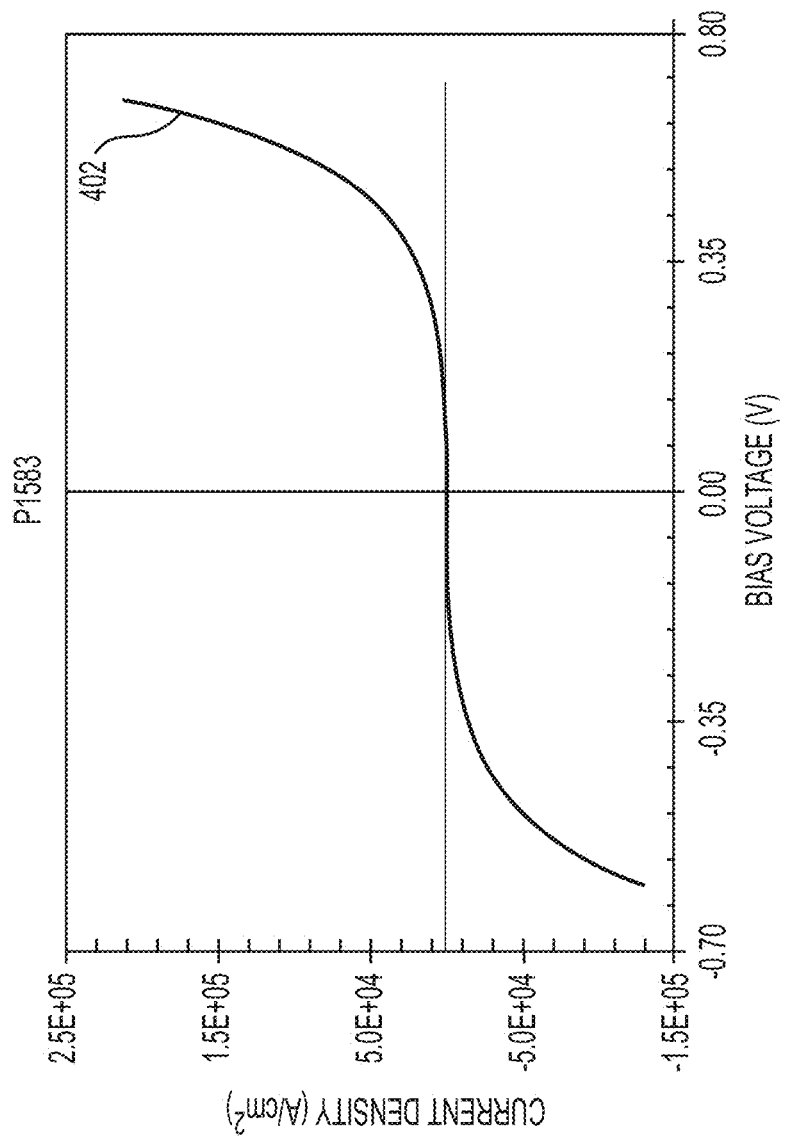
FIG. 4 is a graph showing the I-V characteristic and current density of a MIIM device according to an embodiment of the present invention.

FIG. 4 is a graph showing the I-V characteristic and current density of a MIIM device according to an embodiment. Curve 402 shows current density for a MIIM device according to an embodiment. Curve 402 illustrates that such a MIIM device exhibits both high nonlinearity and low resistance. Such a device can be used at frequencies greater than 1 THz. As explained prior, preferred ACT devices use a double-insulator diode (MIIM). Double insulator diodes provide a greater electrical nonlinearity—and therefore improved responsiveness and NEP—than single insulator MIM diodes. Other devices, such as microbolometers, HgCdTe, and Schottky diodes, can be used in embodiments. While such devices may not be as suitable as MIIM-diode embodiments, they may be used in embodiments where less sensitivity and speed are required.

Embodiments generate interrogating THz pulses to stimulate a process known as coherent bleaching. Coherent bleaching occurs when a medium in which a pulse travels can store energy momentarily before returning it to the pulse via stimulated emission. A pulse with enough energy to cause a state inversion can exhibit coherent bleaching over relatively large distances if its temporal width is shorter than or comparable to the dephasing time of the medium in which it is traveling. The effect of Self-Induced Transparency (SIT), whereby a pulse induces complete transparency in the medium, occurs in the limit that the pulse is much shorter than the dephasing time of the medium in which it is traveling.

FIG. 5 is a set of coupled Maxwell-Bloch equations that can be used to model this region of coherent bleaching in a material. In the coupled Maxwell-Bloch equations shown in FIG. 5, $\mu$ represents the dipole moment of the medium, E is the incident electric field, $\rho_{30}$ is the initial state of inversion for the population, and $\rho_1$, $\rho_2$, and $\rho_3$ represent the dispersive (in-phase) polarization, the absorptive (in-quadrature) polarization, and the inversion parameter of the two-level system approximation of the medium, respectively. The value $\rho_3 = -1$ represents a system where all molecules are in their ground state and $\rho_3 = 0$ is a system that is completely transparent. The pulse attenuates with very little absorption. See, Luvkofsky, David, et al., "Can Precursors Improve the Transmission of Energy at Optical Frequencies?," JOURNAL OF MODERN OPTICS, vol. 56, No. 9, 1083-90 (May 20, 2009), which is hereby incorporated by reference in its entirety, for more details concerning coherent bleaching.

Some common examples of coherent bleaching that occur at lower frequencies than the THz band include nuclear magnetic resonance (NMR) and ground penetrating radar (GPR).

Figure 6:
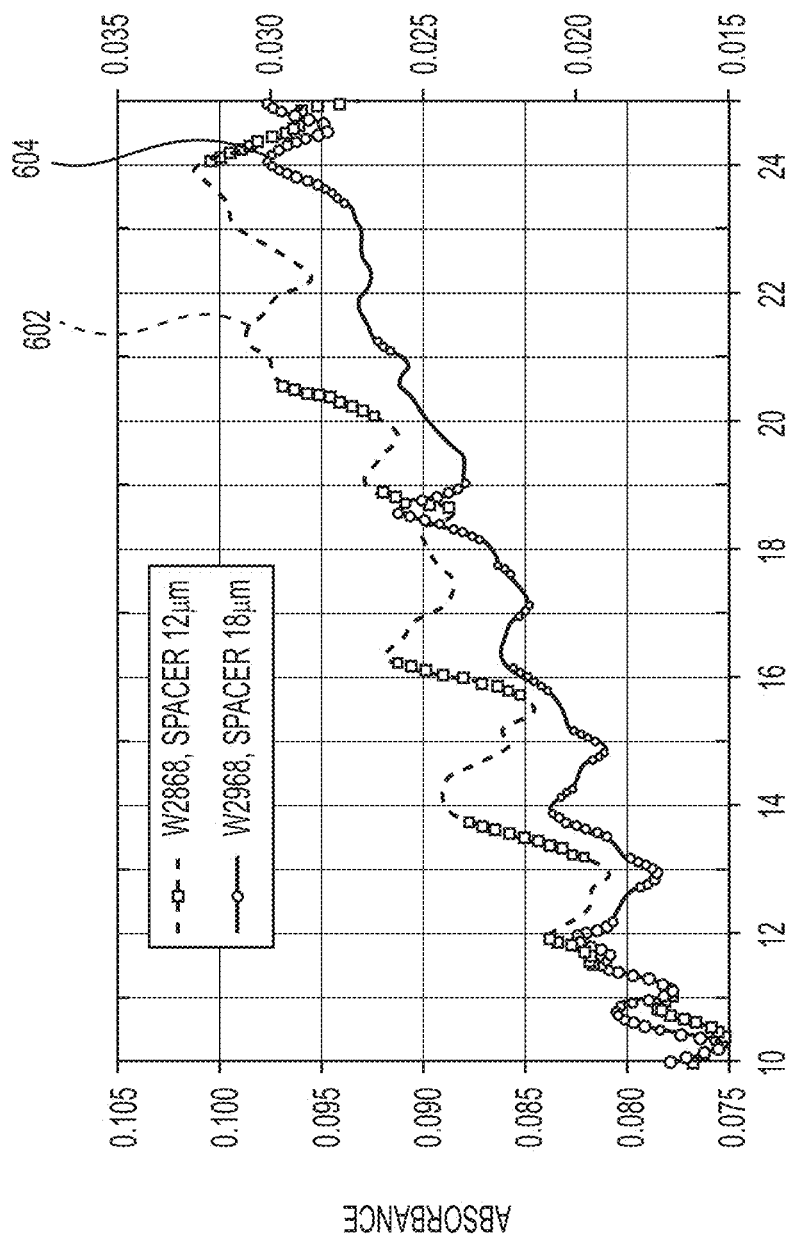
FIG. 6 illustrates simulated application of coherent bleaching to water in the THz frequency band.

FIG. 6 illustrates simulated application of coherent bleaching to water in the THz frequency band. Curve 602 corresponds to W2866, spacer 12 µm. Curve 604 corresponds to W2968, spacer 18 µm. These data indicate there are a number of absorption features (peaks in curves 602 and 604). These absorption features are likely due to molecular vibrations. Theoretical analysis is used to model the conditions required to bleach such a comb of vibrational frequencies.

Figure 7:
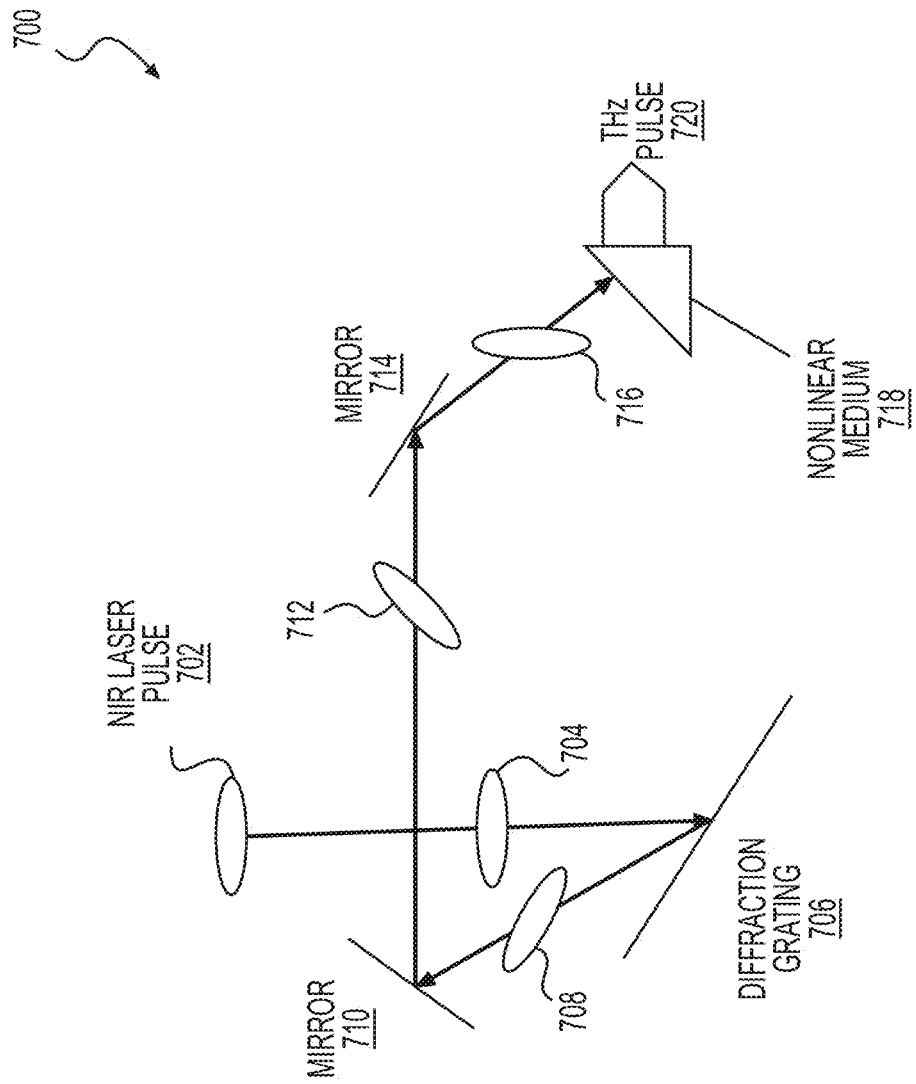
FIG. 7 is a schematic diagram of an exemplary NIR amplifier laser system that can be used as a THz pulse source according to an embodiment.

To achieve coherent bleaching in an embodiment, THz-pulses with approximately 100 femtosecond (fs) duration or shorter and high peak power are generated. FIG. 7 is a schematic diagram of an exemplary NIR amplifier laser system 700 that can be used as a THz pulse source according to an embodiment. As described in more detail below, a laser 702 delivers its energy through a series of lenses (704, 708, 712, 716), mirrors (710, 714) and diffraction grating (706) to a non-linear medium 718 to generate THz waves from the NIR laser's output energy. Such a system can be used as THz interrogation pulse source 104 in FIG. 1 in an embodiment. In an embodiment, laser 702 produces <100-fs, 4-mJ NIR pulses. Using such a laser provides THz peak power exceeding 1 TW/cm$^2$.

The laser-based method is referred to as optical rectification. In an embodiment, optical rectification is performed by generating a THz pulse using a near infrared (NIR) pulse laser 702. The pulse generated by NIR laser 702 impinges a nonlinear medium 718 to induce a short polarization that has the form of the laser-pulse envelope. For sub-picosecond laser pulses, the rectified pulses have a frequency content extending into the THz frequency range. The efficiency of the optical rectification process depends on the properties of nonlinear-medium 718, the phase-matched length of the nonlinear medium 718, and the Intensity, I, of the laser 702. The phase-match length of nonlinear medium 718 is the length where the group index of the MR laser matches the phase index of the THz pulse that is where $n_{THz}=n_v$.

Optical rectification sources pumped by amplified laser pulses with kHz repetition rates are typically on the order of hundreds of pJ. The latter corresponds to a typical NIR-to-THz conversion efficiency on the order of $10^{-2}$. Nonlinear media including Zinc Telluride (ZnTe), Gallium Phosphite (GaP) and Lithium Niobate ($LiNbO_3$) can be used in embodiments as nonlinear medium 718.

To achieve phase matching, in an embodiment, nonlinear medium 718 has a group refractive index for the femtosecond laser pulse that is equal to the phase refractive index for the THz pulse. In a $LiNbO_3$ medium, for example, the optical group and THz phase indexes are such that the THz pulse lags behind the NIR pulse. This limitation can be overcome using a laser pulse with an intensity front that is tilted with respect to its propagation direction.

Figure 8:
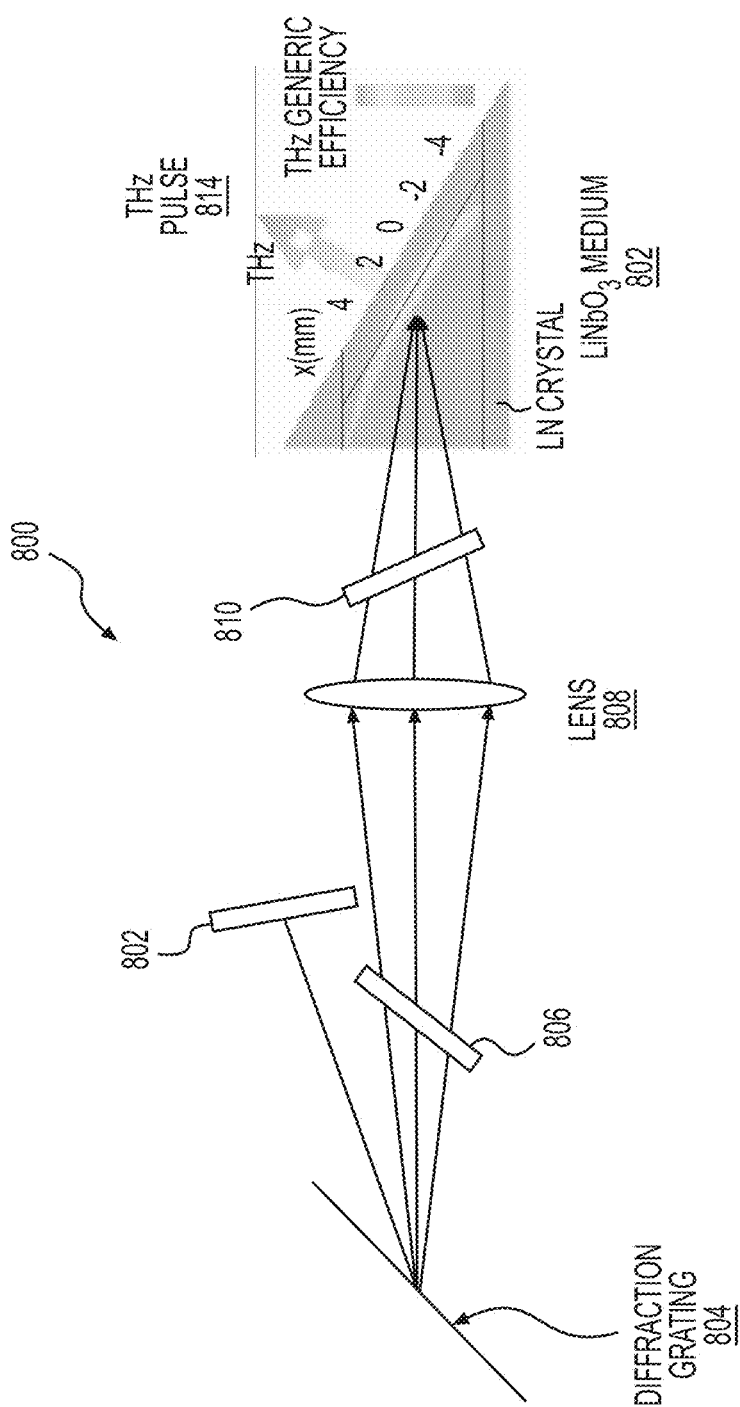
FIG. 8 is a schematic diagram of a laser-based THz system flow of THz current according to an embodiment.

FIGS. 7 and 8 illustrate an exemplary system 700 for generating a THz band pulse according to an embodiment. As previously mentioned, system 700 can be used to generate a THz interrogation pulse source 104 in an embodiment. As shown in FIG. 7, a NIR fs laser 702 generates a pulse that impinges a diffraction grating 706 through a focusing lens 704. The portion of the pulse reflected off diffraction grating 706 is directed through a lens 708 to a mirror 710. Mirror 710 directs the pulse through another lens 712 to a mirror 714. Mirror 714 directs the pulse to nonlinear medium 718 through focusing lens 716. After propagating through nonlinear medium 718, the pulse emerges as THz pulse 720. In an embodiment, nonlinear medium 718 is a wedge LiNbO3 crystal. High NIR-to-THz efficiencies have been measured from this type of crystal. In an embodiment, NIR laser 702 produces <100-fs, 4-mJ NIR pulses resulting in an anticipated THz peak power close to 200 MW. Focusing this THz pulse with a silicon lens to a sub micron size results in a THz-pulse peak intensity 1.1 $TW/cm^2$. In an embodiment, laser system 700 also incorporates an acousto-optics dispersive filter that provides control over the NIR pulse spectrum. Such a filter can be used to tailor the shape and spectrum of the generated THz pulse. This feature might prove useful for exploring the frequency response of the developed detector or mimicking detection scenarios.

Similarly, in FIG. 8, a NIR pulse source 802 emits pulses toward a diffraction grating 804. Diffraction grating 804 redirects the pulses through a lens 808 and optical directional elements 806 and 810 to a nonlinear medium 812. THz pulses are emitted from nonlinear medium 814 as described above.

In another embodiment, THz interrogation pulse source 104 generates THz pulses using an accelerator-based technique. For example, in an embodiment, a variant of the Smith-Purcell free-electron laser (SPFEL) is used. The size of a SPFEL device allows for a portable implementation in an embodiment.

Figure 9:
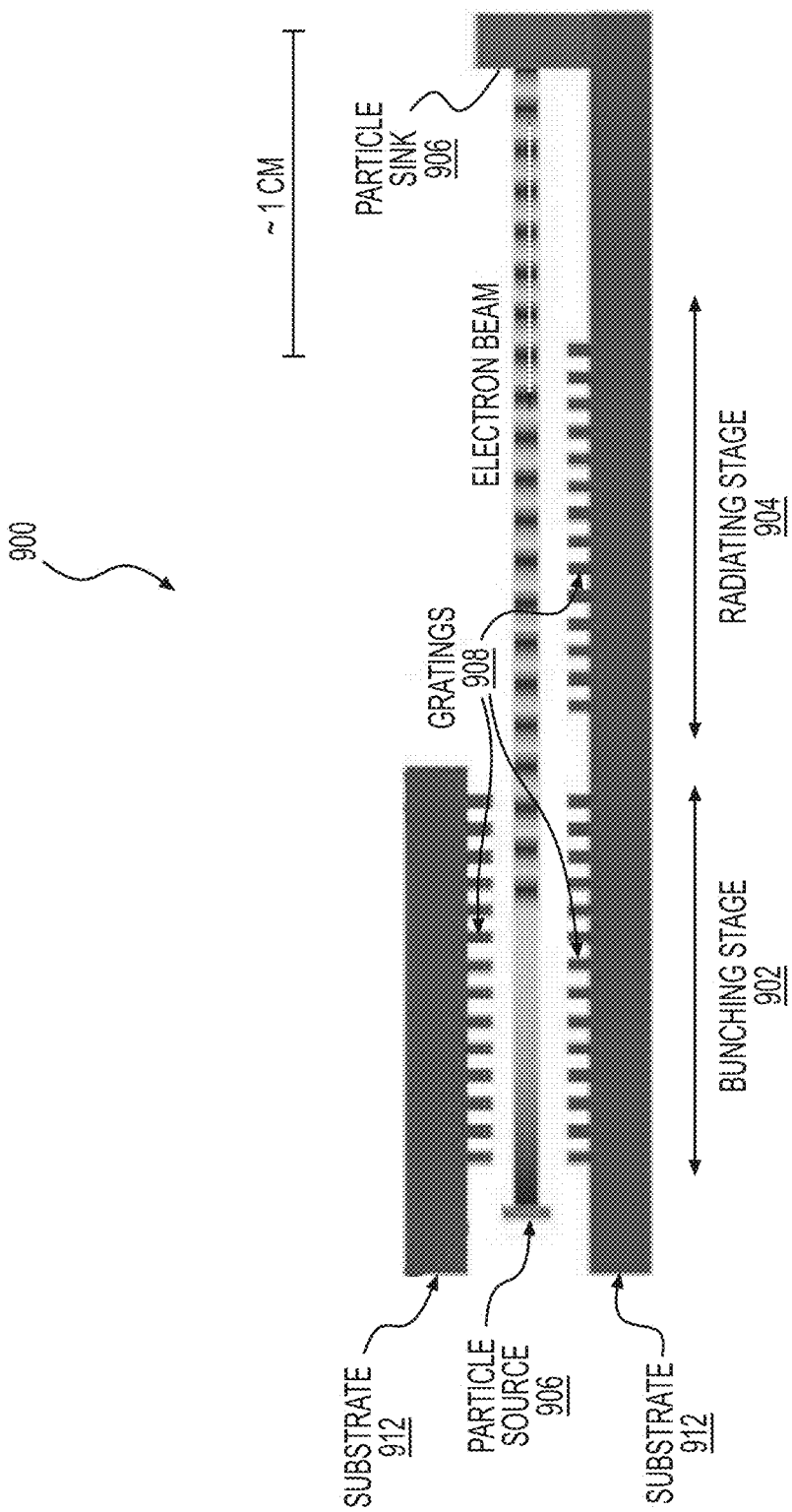
FIG. 9 is a schematic diagram of a two-stage SPFEL THz pulse source 900 according to an embodiment.

FIG. 9 is a schematic diagram of a two-stage SPFEL THz pulse source 900 according to an embodiment. Pulse source 900 can be used as THz interrogation pulse source 104 in an embodiment. In this embodiment, particles emitted from a particle source 906 travel past gratings 908 to a particle sink 910. In an embodiment, gratings 908 and substrate 912 are comprised of metallic boundaries. A low energy (<100 keV) DC sheet electron beam propagates above a periodic metallic structure (e.g., a grating 908 in radiating stage 904) and radiates spontaneous Smith-Purcell radiation.

The electromagnetic fields associated with some spectral orders of the radiation are evanescent and are confined near the structure surface. These are called "surface modes". Some of these surface modes interact with the electron bunch and thereby impart an energy modulation along the bunch with a period corresponding to the strongest surface mode. Because of the low electron velocity, this energy modulation turns into a density modulation at the wavelength of the strongest evanescent mode. This "micro-bunching" of the electron bunch results in an enhancement of emission at a wavelength comparable to and larger than the micro-bunching period. In an embodiment, the SPFEL is operated in a continuous wave (CW) mode thereby producing narrow-band THz pulses. In an embodiment, the THz pulses generated by a two-stage SPFEL THz pulse source produce an average power on the order of Watts. Additional modes of operation may produce short (broadband) THz pulses.

In an embodiment, the electron bunch is compressed at the sub-picosecond level. For example, using a small resonant cavity operating on the $TM_{010}$ mode, the timing of the electric field in the cavity in launching stage 902 is such that the center of the bunch experiences no accelerating field, while the tail of the electron bunch experiences an acceleration, and the head of the electron bunch experiences a deceleration. Because of the sub-relativistic nature of the <100-keV beam, the tail eventually (after a small drift) catches up to the head resulting in an electron-beam bunching. In an embodiment, a 30-fs electron bunch is generated. In an embodiment, the footprint of SPFEL THz source 900 is on the order of 0.5×0.5×0.5 $m^3$.

Coherent bleaching requires THz source 104 to create an extremely short pulse of high peak power and a wide band THz signal. Current THz source technologies include: solid state oscillators, quantum cascade lasers, optically pumped solid state devices, free electron lasers (FEL) and others. As described above, therefore, preferably THz source 104 is a pulsed-laser driven THz emitter or a FEL device.

FEL devices include Klystrons, Travelling Wave Tubes, Backward Oscillators, Gyrotrons and Smith-Purcell FEL devices. While laser-based sources are usable, a bench scale (smaller footprint) device is preferable. For a bench scale device, in an embodiment, the Metal Grating FEL based on the Smith-Purcell effect, described above with respect to FIG. 9, is used.

Other kinds of sources can be used in embodiments to generate the required THz pulses, including but not limited to: optically pumped THz laser, optical rectification, photo-conductive dipole antennae, backward wave oscillator, frequency mixing, and conventional free-electron lasers. In Table 1, the main features of the most popular among these techniques are compared with the characteristics preferred 'Smith-Purcell free-electron laser' (SPFEL) that is described above with respect to FIG. 9.

TABLE 1

Summary of popular coherent THz radiation sources. The last column corresponds to the anticipated performance of the proposed source.

|  | Optically pumped THz lasers | Optical rectification | Photo-conductive dipole antennae | Conventional free-electron lasers | Smith-Purcell FEL |
|---|---|---|---|---|---|
| Average power | >100 mW | ~1 mW | ~1 mW | ~mW | ~mW |
| Frequency range (THz) | 0.3-10 | 0.1-2 | 0.1-1.5 | 0.3-10 | 0.1-10 |
| Tunability of source wavelength | Discrete lines | Not tunable (broadband radiation Δf = 0.5 THz) | Not tunable (broadband radiation Δf = 0.5 THz) | Continuous | Continuous Tunable pulse duration |
| Mode of operation | CW or pulsed | Pulsed | Pulsed | CW or pulses | CW or pulsed |
| Turnkey system | No | Yes | No | No | Eventually Yes |

Because of their relative simplicity, optical rectification or photoconductive dipole switch devices are most popular. In both types of devices, a femtosecond-class laser is used to drive the source.

As described above with respect to FIGS. 7 and 8, in optical rectification, the laser impinges an electro-optical crystal and thereby generates broadband coherent THz radiation. In the photoconductive dipole switch, a split antenna is fabricated on a semiconductor substrate to create a switch. A DC bias is placed across the antenna, and the femtosecond laser is focused in the gap in the antenna. The bias-laser pulse combination allows electrons to jump the gap rapidly, and the resulting current in the antenna produces a terahertz electromagnetic wave. Both of these techniques create THz pulses with duration of ~100 fs; these pulses are always broadband (typically 0.5 THz).

Figure 10:
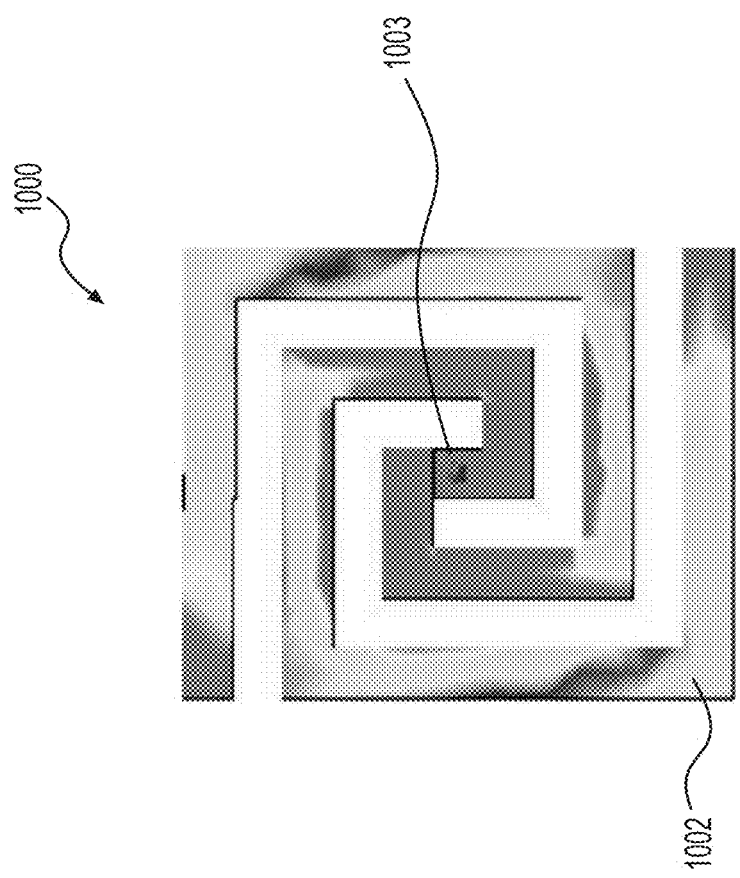
FIG. 10 is a simulated image of an exemplary spiral nanoantenna designed for resonance in the mid-infrared frequency band, with an embedded tunnel diode according to an embodiment.

In an embodiment, the nanoantennas in the ACT devices used in antenna array 110 can be made using frequency selective surfaces (FSS). See, e.g., D. Kotter, S. Novack, W. Slafer, P. Pinhero "Theory and Manufacturing Processes of Solar Nanoantenna Electromagnetic Collectors", The Journal of Solar Energy Engineering, February 2010, Vol. 132 and B. Monacelli, J. Pryor, B. A. Munk, D. Kotter, and G. D. Boreman, "Infrared frequency selective surface based on circuit-analog square loop design," IEEE Transactions on Antennas and Propagation, vol. 53, no. 2, pp. 745-752, February 2005, both of which are incorporated by reference herein in their entireties. Antenna coupled sensors in the infrared range are known. The FSS are comprised of nanoantenna elements scaled in size to the wavelength of energy that is being captured. FIG. 10 is a simulated image of an exemplary spiral nanoantenna 1000 designed for resonance in the mid-infrared frequency band, with an embedded tunnel diode 1003 according to an embodiment. Other antenna types may be applicable according to an embodiment.

Device resonance in antenna 1000 is caused by the wavelike properties of electromagnetic radiation absorbed by a metal antenna. The basic theory of operation is as follows. The incident electromagnetic radiation (flux) from a THz or thermal source excites plane-wave electrical currents in microantenna structure 1000. When antenna 1000 is excited into a resonance mode it induces the plasma release of electrons from the metal antenna arms 1002. The electrons freely flow along the antenna generating current at the same frequency as the resonance.

FIG. 10 also shows that current flows toward the antenna feed point. The electric field is clearly concentrated at the center feedpoint. This provides a convenience point to collect energy. FIG. 2 also demonstrates the ability to embed a diode into the feedpoint of the antenna structure for rectification and signal processing. In an embodiment, rectification is performed using a metal-insulator-metal (MIM) tunneling diode. Other diodes, such as MIIM diodes can be used in embodiments, and may provide better performance. To achieve the required THz switching speeds, diodes require highly nonlinear current-voltage characteristics, sharp turn-on, and very low dark current. In an embodiment, these requirements are achieved through use of asymmetric diode contact metals and energy band engineering of the tunneling insulator layers.

For example, as described above, in an embodiment, diodes with two insulators are used as they can provide additional non-linearity over single insulator MIM diodes. The multiple insulators (MIIM) induce resonant structures that support high-energy tunneling. As shown in FIG. 4, the devices also may exhibit a negative differential resistance (I-V) curve behavior. In an embodiment, negative differential mobility is induced in the MIIM diodes. Diodes with negative resistance enable the implementation of solid-state oscillator circuits in the 0.1-2 THz region. In turn, this provides increased sensitivity of detection as well as low power, compact sources for active interrogation.

Figure 11:
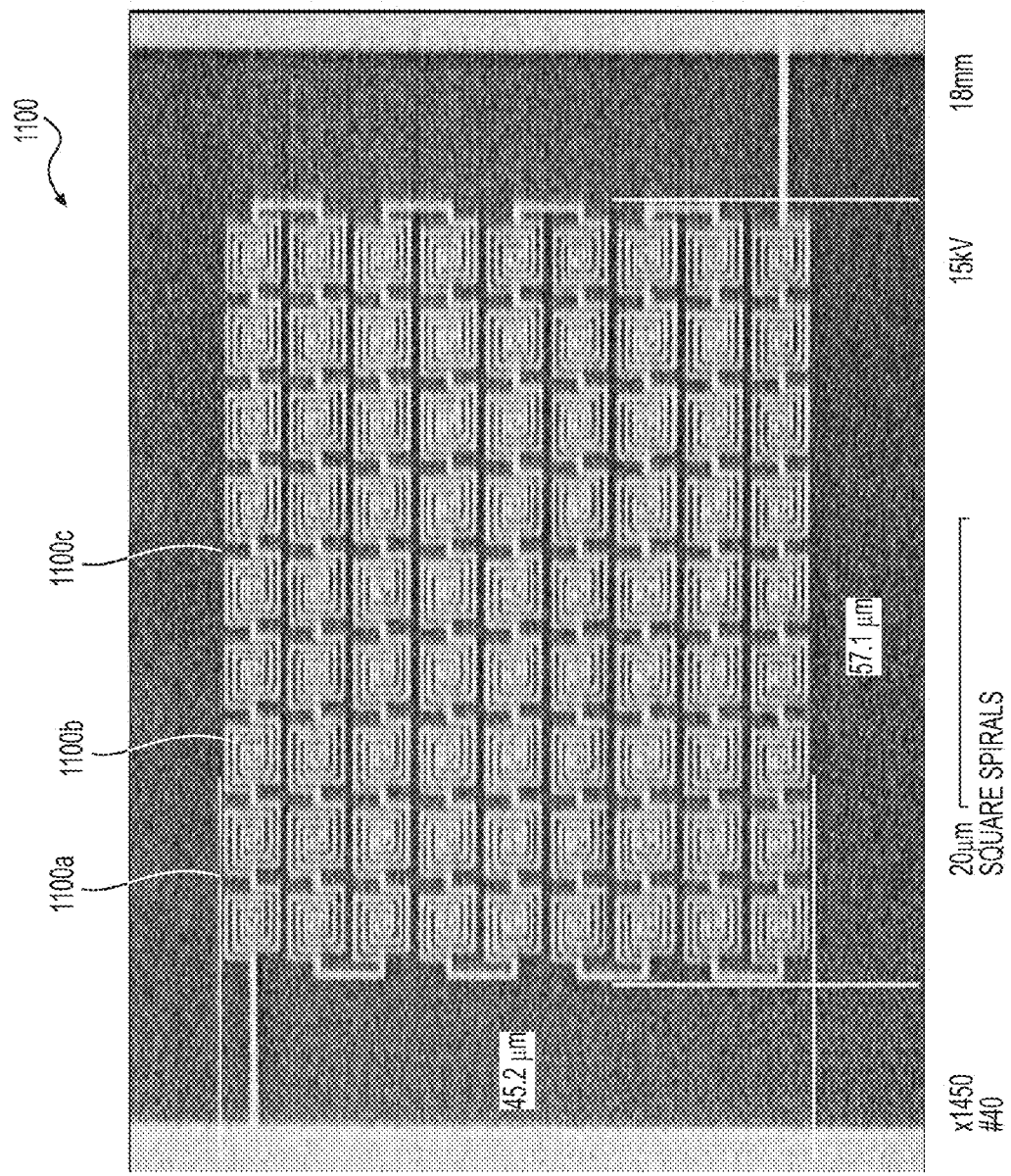
FIG. 11 is a scanning electron microscope picture of an exemplary antenna array 1100 according to an embodiment.

Spectra from materials, such as explosives and other contraband, have several absorption peaks at unique frequencies. In an embodiment, discrete antenna elements are tuned for selectivity to each peak. FIG. 11 is a scanning electron microscope picture of an exemplary antenna array 1100 according to an embodiment. Although not illustrated, the array can be ganged into subarrays of multiple antenna elements to optimize reception of a THz signal and to improve SNR.

In antenna array 1100, discrete antennas, such as antennas 1102a, 1102b, and 1102c, are configured into periodic arrays comprising a frequency selective service (FSS). Resonant frequency and spectral bandwidth of the FSS are controlled by the geometry of the periodic metallic antenna structures and the refractive index of associated thin film materials. The FSS acts like a physical template that passes only electromagnetic energy representative of a particular material of interest, such as an explosive. It also provides cold filter rejection of broadband thermal background noise. The use of a FSS nanoantenna array provides unprecedented narrow band THz discrimination with tunable selectivity to absorption lines of pre-defined chemical species. This enables positive identification of threats and greatly reduces false negatives.

As described above, in an embodiment, detection of a material of interest occurs by detecting THz excitation pulses reflected from an object under surveillance. However, signal scattering is likely to occur that reduces coherence. To minimize the effect of scattering, in an embodiment, the detector is configured as a phased array to increase the field-of-view and to maximize capture of the retro-reflected signal.

When a THz interrogation pulse illuminates materials high in hydrogen content, such as explosives or other contraband, the pulse reflected from the illuminated material is modified due to resonant material absorption. The modified reflected pulse appears to be "ringing." This ringing effect arises from a number of factors including: absorption in the atmosphere, propagation effects from a skin boundary, propagation effects from a media/tissue boundary, and absorption from materials of interest, such as explosives. In an embodiment, this modification of the interrogating THz pulse serves as a "fingerprint" that can be used to identify the material under investigation.

In an embodiment, a series of FSS detectors perform single-point absorption peak measurements and matched-filter analysis of the reflected signal generated by the interrogation signal. As a result, scanning of the full spectrum and FFT post processing of datasets are not required. Each antenna in the nanoantenna array, such as nanoantenna array 1000, is "tuned" to a selective band pass that represents a unique spectral absorption peak of the explosive material, or other contraband. As a result, embodiments allow real time response and multiple measurements in a variety of acquisition modes including passive scanning.

As described above, data analysis is used to extract unique spectral features, including: frequency of absorption peaks, peak widths, ratio between peak heights and peak slope. These features serve as discriminators or "fingerprints" of materials under investigation. In an embodiment, pattern classification algorithms match spectra to a database of validated spectra. Matches indicate a presence of the matched material.

In an embodiment, THz device components are fabricated using polymer composites. In an embodiment, component fabrication relies on characterization of the polymer composites using a method to characterize the spectral properties of the media. An exemplary way to characterize the properties of the media is to use THz time domain spectroscopy (THz-TDS). THz-TDS has been widely used to extract frequency dependent optical properties in the THz region.

Figure 12:
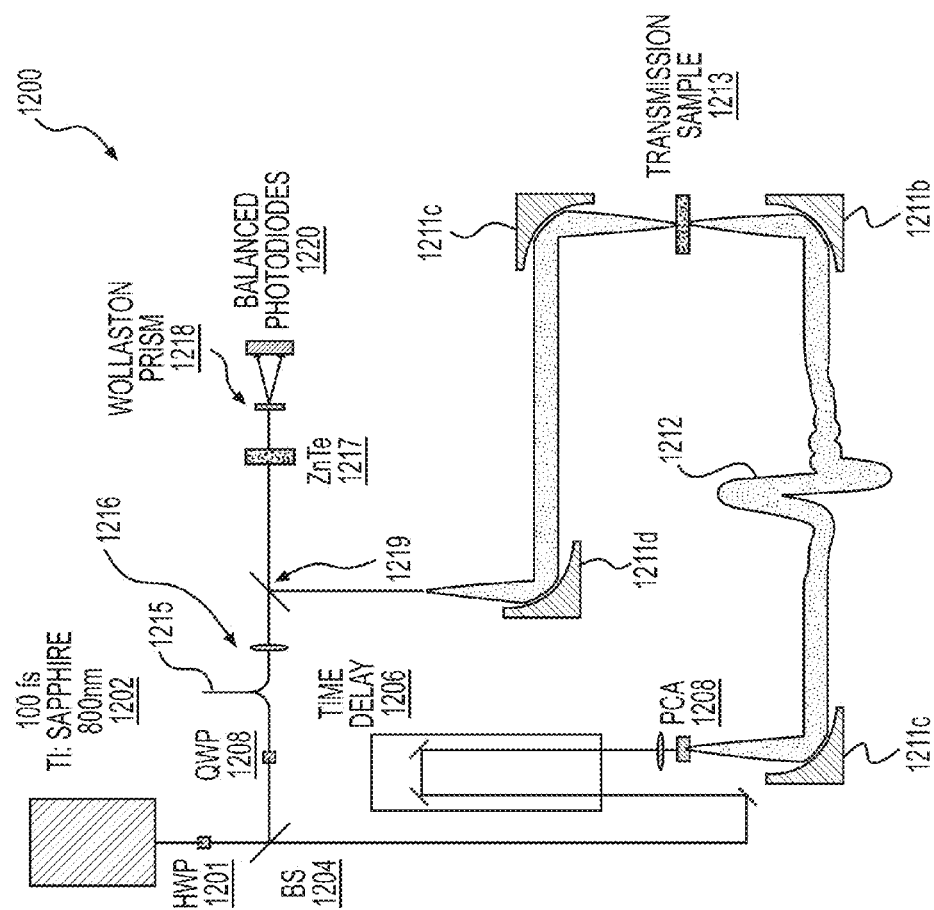
FIG. 12 illustrates an exemplary THz-TDS system 1200 for characterizing polymer composites.

FIG. 12 illustrates an exemplary THz-TDS system 1200 for characterizing polymer composites. As time delay 1206 moves it changes the position of the THz waveform with respect to a probe beam pulse 1215 as they both arrive at the crystal (ZnTe) 1212. The entire THz waveform is extracted by moving the time delay while collecting THz electric field data at every position surrounding the pulse.

As shown in FIG. 12, a Ti:Sapphire laser source provides a pulse through a half-wave plate 1201 to a beam splitter 1204. Beam splitter 1204 splits the pulse signals and directs a portion to a time delay 1206 and a portion to a quarter-wave plate 1204. Pulse 1215 goes through lens 1216 to a ZnTe crystal detector 1217 through a pellicle 1219. Time shift 1206 adds delay to the pulse path. Incremental delay over the entire time from of the pulse allows collection of THz field data at each incremental point around the THz pulse. The time shifted pulse is passed through a lens 1208 to a photoconductive antenna 1210. Photoconductive antenna 1210 emits a THz pulse 1212 that is directed by parabolic mirrors 1211a and 1211b through a transmission sample 1213. Transmission sample 1213 is a sample of the nonlinear material whose optical properties are desired to be characterized. THz pulse 1212 is then directed by parabolic mirrors 1211c and 1211d to pellicle 1219, which reflects THz pulse 1212 to detector crystal 1217. THz pulse 1212 alters the birefringence properties of detector crystal 1217, which, in turn, alters the phase characteristics of co-propagating pulse 1215. A Wollaston prism 1218 separates pulse 1215 into its orthogonal components and directs each of the orthogonal components to one of a pair of balanced diodes 1220. Because a phase delay is introduced to pulse 1215 by the effect of the THz pulse on the birefringence of crystal 1217, the relative amplitudes of the orthogonal components of pulse 1215 are changed, which serves as a measure of the magnitude of the THz pulse 1212.

Figure 13:
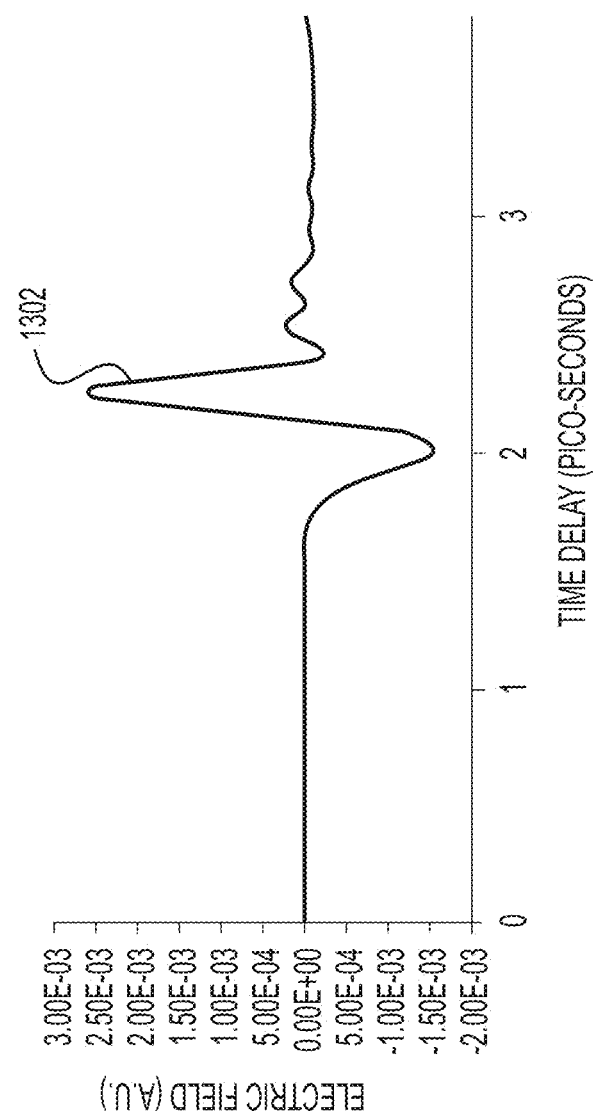
FIG. 13 illustrates an exemplary THz waveform measured through air.

FIG. 13 illustrates an exemplary THz waveform 1302 measured through air. Waveform 1302 represents a THz pulse traveling through air with no sample in the pulse's path. As such, waveform 1302 can be used as a baseline or reference for determining the response of the THz pulse when interrogating a material of interest.

Figure 14:
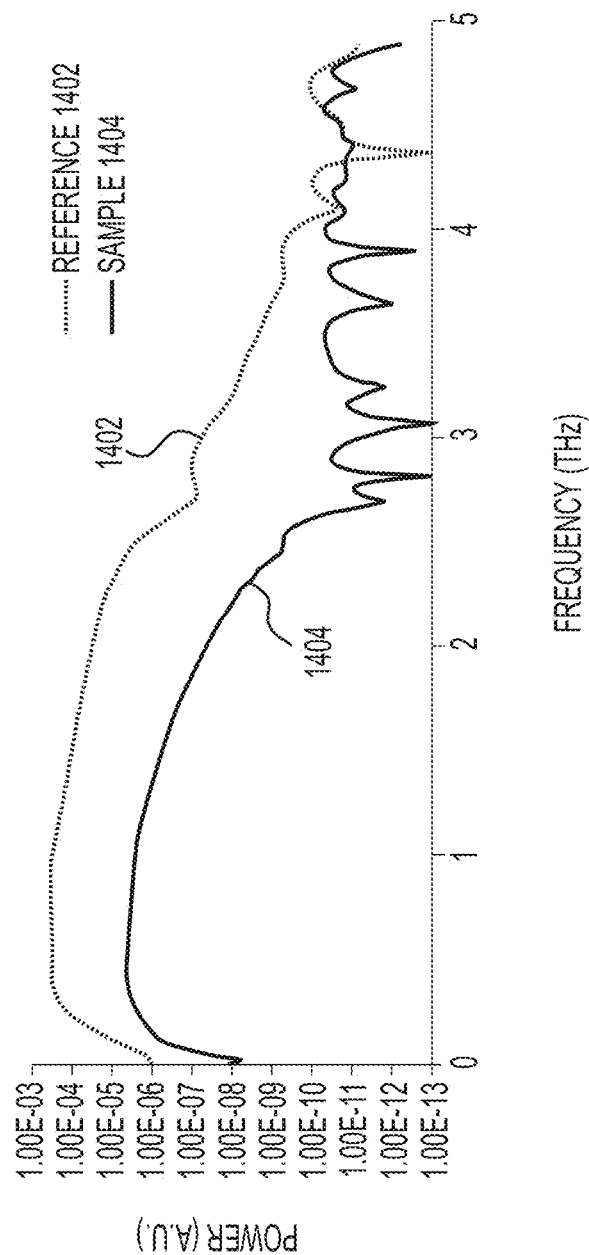
FIG. 14 is a graph illustrating exemplary spectral power magnitude curves for an exemplary sample pulse and an exemplary reference pulse.

To calibrate optical properties using a THz-TDS system, a transmission sample 1213 of known THz optical properties is probed. Time-delay data from each probe is collected and transformed from time domain to the frequency domain. For example, in an embodiment, the transform from the time domain to the frequency domain is performed using a discrete Fourier transform algorithm known as the fast-Fourier transform (FFT). Applying the FFT to the time-delay data THz spectral data provides the magnitude and phase of the THz electric fields. FIG. 14 is a graph illustrating exemplary spectral power magnitude curves for an exemplary sample pulse (curve 1404) and an exemplary reference pulse (curve 1402).

The power and electric field strength axes shown in both the frequency (FIG. 14) and time domain (FIG. 13) graphs are in arbitrary units (a.u.). By using optical transfer functions, the ratio of the complex spectrums of the reference and sample can be directly related to the frequency-dependent complex index of refraction, n, where n=n+ik and n is the real part of the refractive index and k is the extinction coefficient representing absorptive loss. From an electronics perspective, the frequency-dependent dielectric constant, $\in$, is a more desired quantity. Dielectric constant $\in$ relates to the complex refractive index by $\in=(n+ik)^2$.

The refractive index and extinction coefficients can be calculated analytically only if the absorptive loss of the sample is small enough to make k negligible for portions of the optical transfer function. However, because of the sensitivity of the model to slight variations in the complex refractive index, a more precise approach is used. The more precise approach, known to those skilled in the art, involves breaking down the complex equation into real and imaginary parts and solving a binary equation at each frequency point. The resolution for the complex refractive index needs to be large to again help ensure modeling precision. This requires iteratively solving binary systems of equations. The difference in refractive index and extinction coefficients solved by the simplified analytical method and the iterative method can be seen from FIGS. 15 and 16.

Figure 15:
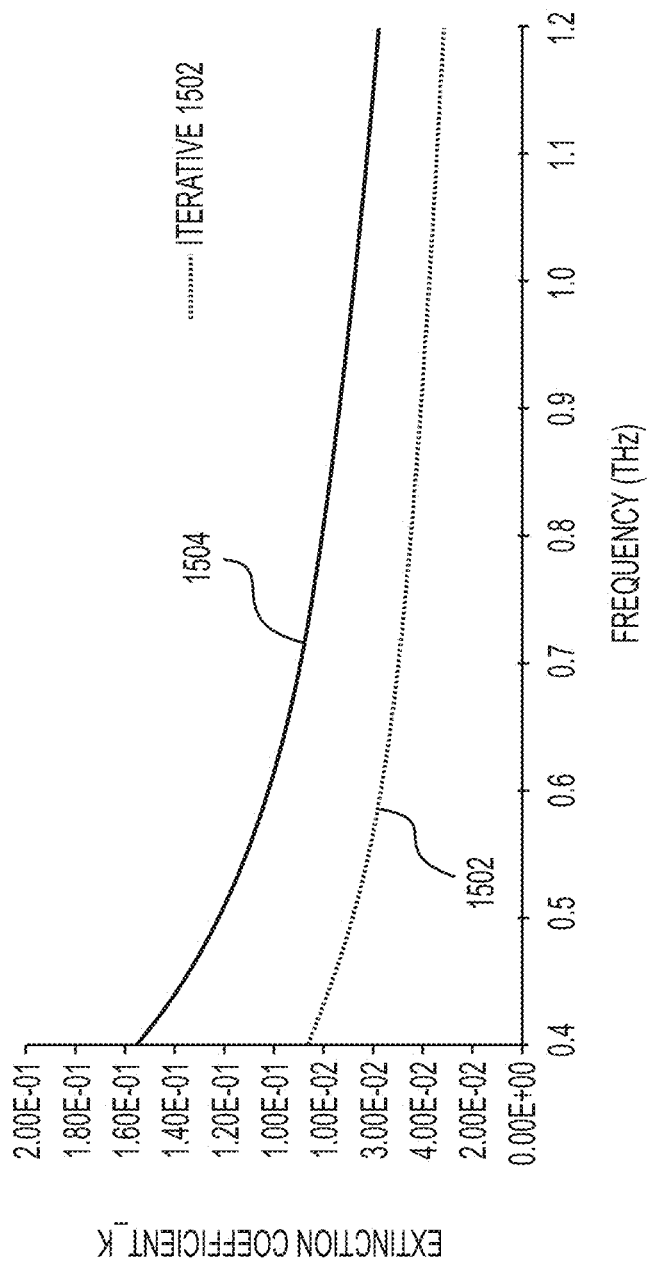
FIG. 15 is a graphical representation of the refractive index calculated using both an iterative technique and an analytical approach.
Figure 16:
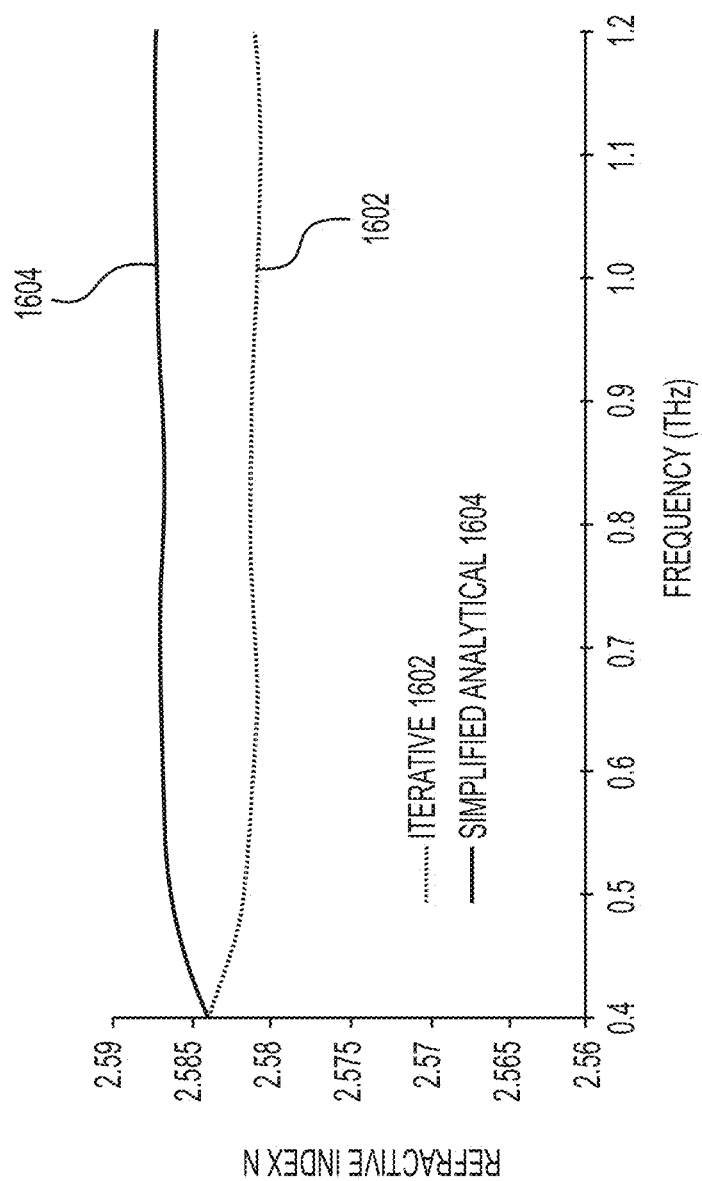
FIG. 16 is a graphical representation of the extinction coefficient determined using the iterative and analytical approaches.

FIG. 15 is a graphical representation of the refractive index calculated using both the iterative technique and the analytical approach. FIG. 16 is a graphical representation of the extinction coefficient determined using the iterative and analytical approaches. As shown in FIGS. 15 and 16, both the refractive index and the extinction coefficient change appreciably when calculated by the more accurate iterative technique. In FIG. 15, curve 1502 is calculated using the iterative approach and curve 1504 is calculated using the analytical approach. In FIG. 16, curve 1602 is calculated using the iterative approach and curve 1604 is calculated using the analytical approach.

Features of a THz detection system according to an embodiment include that the response is not thermal time-constant limited as compared to bulk bolometer detectors. Laser 1 k/s duty cycle and 1 ps ACT detector response sustains less than 10 sec interrogation rates and achieves an order of magnitude improvement in SNR.

Further, a system according to an embodiment provides inherent polarization selectivity of antenna-based detectors. Antenna geometry dictates the preferential polarization orientation of detector sensitivity. Bulky and expensive optics are not required to detect specific polarization of incident radiation.

In addition, a detector according to an embodiment provides for multi-band operation. The detector uses discrete, tuned resonant antenna elements. Arrays of multiple antenna sub-arrays can be configured to concurrently detect multiple spectral features (resonant peaks) of explosives or other material of interest. This greatly increases system response time and reduces false alarms.

Referring back to FIG. 1, an exemplary graphical representation 110d illustrates THz spectral peaks of interest output or registered by sensors in antenna/diode detector array 110. The spectral data represents the possible presence of explosive materials within the field-of-view of the THz Imaging System 100 due to the spectral energy at 2.0 THz.

However, it should be understood that the shape of the response curve 110d representing spectral peaks of explosive material can be further modulated by several factors including noise introduced by propagation of interrogation pulse 106 through various mediums and impacts of high water content within the object under interrogation 108. To compensate for the effects of such noise, advanced data analysis methods are required to filter and compensate for noise and to extract out unique features representative of threat materials.

Exemplary data analysis methods comprise detection and classification methods that increase the operational capabilities and selectivity of system 100. An exemplary data analysis method according to an embodiment is termed the feature extraction method. The feature extraction method extracts features from the output of antenna/diode detector array 110 that are unique to materials of interest, such as explosives. Examples of extracted features, include: 1) a spectral fingerprint in the frequency domain for each sensor; 2) a total power value of the signal detected by each sensor; and 3) time domain data for each spectral fingerprint that represents peak rise time, peak shape/slope, and time correlation to the interrogation pulse.

Still referring to FIG. 1, in an embodiment, data acquisition and statistical analysis module 112, performs data acquisition using analog to digital conversion hardware such as sample and hold circuitry, ADC converters, phase-lock loops, PLL and other methods apparent to those skill in the art. In an embodiment, all analysis of spectral peaks is performed using digitized data.

In an embodiment, a point-by-point Fast Fourier Transform (FFT) is performed on the gradients of the curve for each sensor. The FFT computation provides FFT values for each sensor as a function of frequency (in the frequency domain). Still referring to FIG. 1, data acquisition and statistical analysis module 112, "power in the signal" is computed for each sensor using the reverted FFT values. This computation is performed by determining the area under the response curve. That is, integrating the function of the response curve.

Still referring to FIG. 1, data acquisition and statistical analysis module 112 identifies a portion of time within the period of time that represents when the peak value of 110d occurs and correlates it to interrogation pulse event 104.

It should be understood that for successful classification, acquired signals or data must contain information characteristic of the object being sensed or detected. Moreover, methods have to be available to extract the characteristic information from the signals or data. The characteristic information must be unique, reproducible and readily processed by the pattern classification methods 114. Exemplary embodiments of the pattern classification methods according to various embodiments of the invention use quantitative anomaly detectors and physics-based discrimination schemes to distinguish between threatening and non-threatening objects.

The acquisition of real-time data from sensors and subsequent data reduction/summarization methods will be employed. Various embodiments of the "pattern classification methods" use aspects of the following data analysis methods:

Primary resonant frequency of spectral peak
Secondary resonant frequency peaks
Standard power density features (one per sensor);
Standard deviation and mean values of overall raw sensor data.
Statistical methods to derive peak shape including rise time, slope, peak width at half power point.

In an embodiment, pattern classification module 114 uses a fusion of methods to perform near-real time identification of threats. In one embodiment of the invention, for example, the following exemplary analysis methods are fused: i) time domain feature extraction; ii) wavelet analysis; iii) matched filter detection; and iv) model-based frequency analysis. The values derived or computed from these exemplary analysis methods are further processed, for example using fuzzy logic, to increase the probability of accurate classification.

Pattern classification methods begin by gathering raw sensor data, for example, from security screening system 100. Raw data is obtained from sensors 110 and represented as spectral waveforms. The data is acquired at user selectable sample rates. Sensor-level digital signal processor (DSP) firmware extracts features and patterns from the raw spectral data. Additionally, the extracted features and magnetic patterns can be further post-processed by a standard desktop or laptop computer using custom software.

The extracted features and patterns from each sensor of security screening system 100 are analyzed as groups to provide additional information, such as multiple absorption peaks representative of a particular type of explosive and/or ratio of peak amplitudes representative of explosives.

For the following described exemplary methods of the invention, it should be understood that "features" or "feature extraction" is defined as "repeatable characteristics in the raw data that are consistent for the same group or class of detectable threat objects." According to various embodiments of the invention, the features are available in the time domain, the frequency domain, and the two frequencies combined, that is, the time/frequency domain.

Accordingly, in one embodiment of the invention, a pattern classification method uses a fusion of classification analytical methods to improve the signal-to-noise performance of sensors and to extract unique spectral features.

Specific classification analysis methods include: wavelets, matched filters and model-based frequency analysis.

One exemplary embodiment of a classification analysis method according to the invention is a wavelet method. The wavelet method provides the means to extract secondary or complex spectral features. The exemplary wavelet method allows the simultaneous extraction of both primary resonant frequencies and secondary harmonic signals having different frequency resolutions. Additionally, the wavelet method preserves the timing information (time domain) of the signal that other data analysis methods fail to maintain. The wavelet method is dependent upon deriving a waveform transform that best matches the signal characteristics of the object being analyzed (for example, TNT explosive). The function of the wavelet method provides a "best fit" of the wavelet to the pertinent portions of the theoretical absorption features of materials that comprise the threat object.

Wavelets derived from the wavelet method are well suited for the analysis of predominately non-stationary signals that have sudden spikes or peak values and a transient existence. The wavelet method uses wavelets for feature extraction. That is, the numerical implementation of the wavelet transform is a filter bank designed for processing of signals that have a short duration (transient). The wavelet transform uses a correlation operation to compare real-time signals to an elementary function. The wavelet transform compares the response signal to a pre-defined set of short waveforms called the fundamental wavelet (or mother wavelet). The wavelets have different time durations, or scales, that mathematically represent impulse-like functions. This enables near real-time processing of impulse signals, such as induced coherent bleaching effects.

The wavelet transforms of the wavelet method indicate the frequency of the signal and indicates the timing of when the frequency occurs. That is, the wavelet method applies wavelets to characterize a signature simultaneously in both the time and frequency domains. Accordingly, the wavelets are used to:

1. detect unique spectral signal responses, such as a nonlinear transients, spectral crossover or inflection points which may represent ringing and distortions from noisy medium such as water;
2. remove undesirable trends from the signal, such as noise from THz source or environmental noise artifacts; and
3. suppress random, but well characterized, noise sources such as thermal background and electromagnetic interference.

Typical detrending techniques use low-pass filters, which can also impact or alter desired signal features. However, wavelet-based detrending preserves the important features of the original signal.

In real-time, the signature of a potential threat object is acquired, such as, during the period of time a person/item is at a security checkpoint. Although various materials of interest, such as explosive, generate a unique spectral signature or response, other benign materials also have overlapping spectral signatures. The uniqueness is not readily apparent with analysis methods which use only one basis function (complex sinusoidal). The wavelet method reduces to practice a series of "mother wavelets" that are tailored to match the threat signals of interest.

Another exemplary embodiment of a classification analysis method according to the invention comprises a matched filter method. The matched filter method provides a technique to filter out typical "false alarm" noise responses. The matched filter method looks at measured spatial data. The results are compared to modeled data.

A matched filter can be used to "match" a particular transit spectral waveform to achieve the maximum signal to noise ratio (SNR) and to emphasize certain signal bands where high fidelity information is present while deemphasizing regions that are more prone to noise corruption.

Another exemplary embodiment of a classification analysis method according to the invention is a model-based frequency analysis method (super-resolution). Often important features of the spectral response are not evident in the time waveform of the signal. Therefore, the resolution of this frequency response is difficult to resolve and to acquire the important features of the responses for additional processing and/or analysis. The model-based frequency analysis method is a model-based analysis technique to improve resolution, and includes using the following various methods: matrix pencil, covariance, prong's method, and principle component auto-regressive (PCAR).

In an embodiment, the frequency analysis method is based on the "matrix pencil" method. Using the matrix pencil method, the magnetic response will be modeled as a time series and approximated with a recursive difference equation. The mathematical equations and derivative of the matrix-pencil method would be well known to those skilled in the art. The matrix pencil method quantifies the resonance frequency and the primary frequencies where the power of the signal resides. The matrix pencil method is also optimized to obtain a super-resolution power spectra even when only small data sets are available.

In another exemplary embodiment of the pattern classification method 114, the validation is performed through the use of fuzzy logic rules. Fuzzy logic is a problem-solving control system methodology and is implemented, for example, by software. Fuzzy logic provides a simple way to arrive at a definite conclusion based upon sometimes vague, ambiguous, imprecise, noisy, or missing input information. Fuzzy logic methodology is an approach to control problems by mimicking how a person would make decisions, only much faster. Fuzzy logic incorporates a simple, rule-based, IF X AND Y THEN Z, approach to solving a control problem rather than attempting to model a system mathematically. The fuzzy logic model is empirically-based relying on an historical knowledge and experience. Fuzzy logic can process nonlinear systems that would be difficult or impossible to model mathematically. An exemplary fuzzy logic explores relationships between multiple data inputs to reach empirical conclusions. For example, in one embodiment, fuzzy logic is used to assign different weights to spectral features such as slope, rise time, magnitude, and peak shape of the spectral response. Fuzzy logic is also used to weigh the confidence level of the classification decision.

Still referring to FIG. 1, raw sensor data is outputted from respective sensors 110c wherein the raw data is analyzed in a time domain 112, a frequency domain 112, and a joint time domain.

After validation by the fuzzy logic of all the inputs, the empirical conclusions are inputted from fuzzy logic to a neural network for further processing. Each of the extracted spectral features or characteristics are assigned weight values by the probabilistic neural network. The neural network compares the real-time spectral response to a prior trained database of known threat signature features. False alarms are greatly reduced and potential threats are identified and assigned a level of probability of being a threat.

A detector according to an embodiment can operate in an uncooled environment at atmospheric pressure.

In an embodiment, antenna/diode detector array 110 functions as an imaging device. In an embodiment, the 'core' nanoantenna technology is scaled to implement imaging applications. In an embodiment, each antenna/diode element in antenna/diode detector array 110 serves as a pixel in an imaging array. For example, a 320×240 pixel array, with associated data acquisition hardware (or firmware or software), can be used to digitize a terahertz image. The response time of the rectifier is more than adequate to sustain a 30 Hz frame rate that is required to provide real-time imaging.

Figure 17:
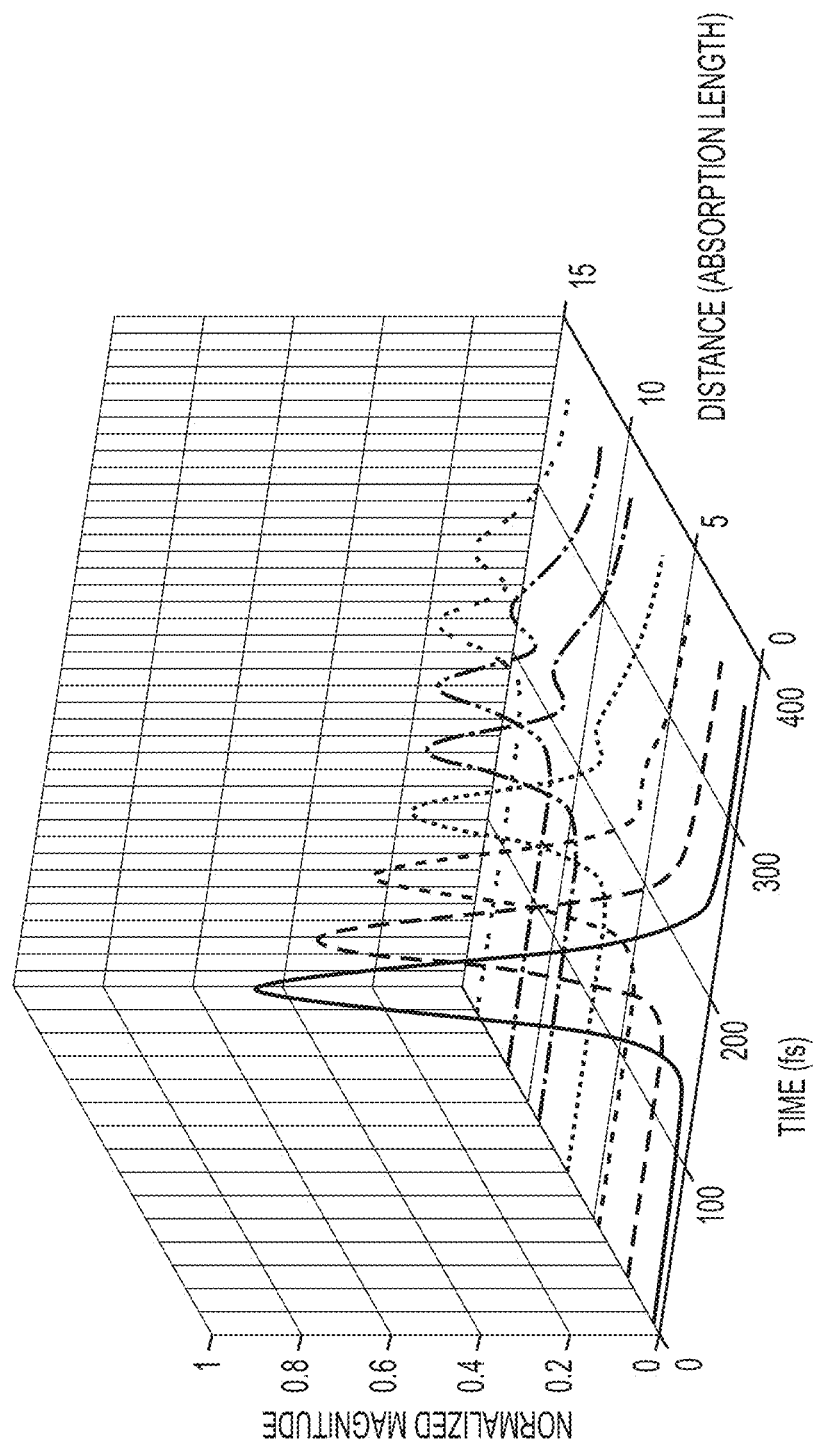
FIG. 17 is a graph that illustrates the absorption characteristic of a weak THz pulse (2.3 W/cm$^2$) as it propagates up to 15 absorption lengths through a coherent medium.
Figure 18:
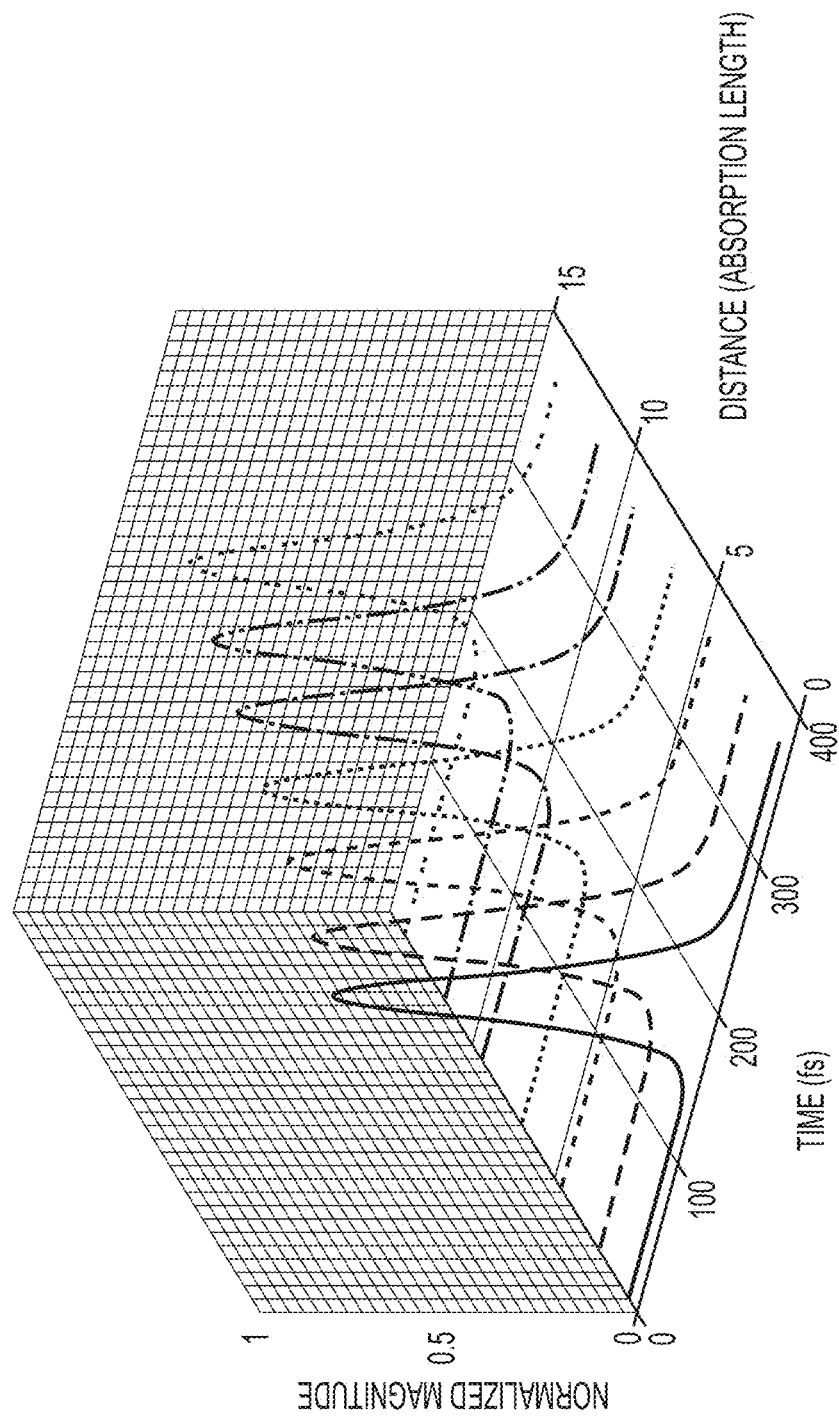
FIG. 18 is a graph that illustrates the absorption characteristic of a high power pulse (peak intensity 760×10$^9$ W/cm$^2$) as it propagates up to 15 absorption lengths through a coherent medium.

FIG. 17 is a graph that illustrates the absorption characteristic of a weak pulse (2.3 W/cm$^2$) as it propagates up to 15 absorption lengths through a coherent medium. FIG. 18 is a graph that illustrates the absorption characteristic of a high power THz pulse (peak intensity 760×10$^9$ W/cm$^2$) as it propagates up to 15 absorption lengths through a coherent medium. In FIG. 18, the high power of the pulse in a short time compared to the medium coherence time inverts resonance such that absorption is reduced to almost 0.

Figure 19:
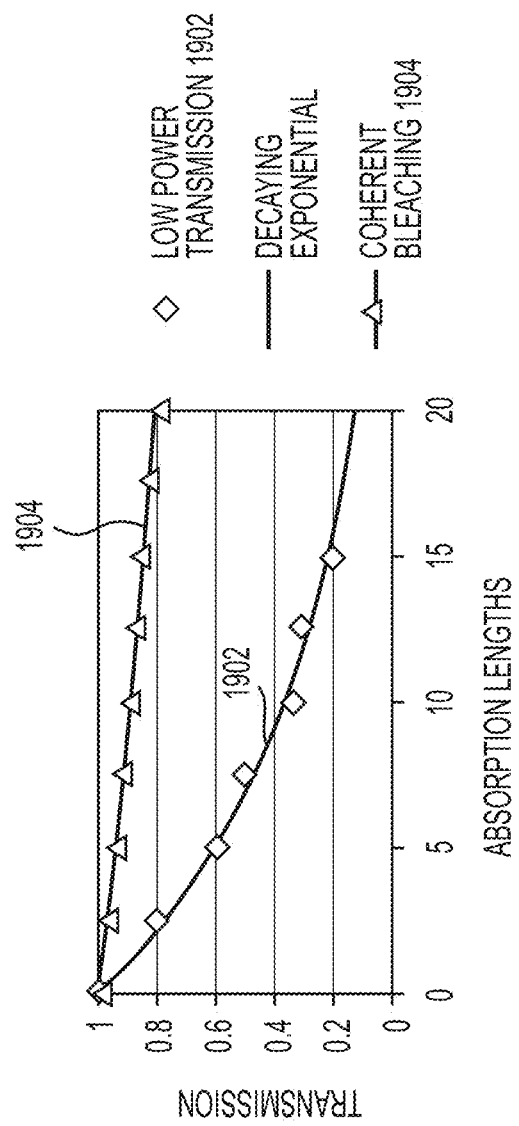
FIG. 19 is a graph that shows the peaks of the pulses illustrated in FIGS. 17 and 18 plotted as a function of distance.

FIG. 19 is a graph that shows the peaks of the pulses illustrated in FIGS. 17 and 18 plotted as a function of distance. In FIG. 19, curve 1902 corresponds to the pulse propagation absorption profile without coherent bleaching shown in FIG. 17, and curve 1904 corresponds to the pulse propagation absorption profile with coherent bleaching shown in FIG. 18.

As can be seen from curve 1904, the transmission with distance drops off exponentially at low power. An exemplary absorption profile for a high-power short THz pulse is shown in FIG. 6. The pulse response illustrated in FIG. 6 is for a pulse having a peak intensity of 760×10$^9$ W/cm$^2$. The high power within a time shorter than the coherence time inverts resonance such that the absorption is reduced almost to zero. This is the result of coherent bleaching. The bleached absorption coefficient $\alpha_B$ is calculated for this example using the data of FIG. 5, which shows that the pulse is decreased by ~1% per absorption length, defined as $L_\alpha = 1/\alpha$, where $\alpha$ is the initial unbleached absorption. Thus, the total absorption A in length $L_\alpha$ is $A=1-\exp(-\alpha L_\alpha)=1-\exp(-\alpha_B/\alpha) \approx \alpha_B/\alpha$.

This absorption approximation is valid because the loss is very small in one absorption length. Thus $\alpha_B/\alpha=0.01$, which means that the bleached absorption is $\alpha_B=0.01\alpha$, i.e., the bleached absorption coefficient is 1% of the low-power absorption coefficient. At 0.8 THz, the low-power absorption coefficient is $\alpha=150$ cm$^{-1}$, as shown in the literature. Consequently, the bleached absorption coefficient $\alpha_B=1.5$ cm$^{-1}$.

For substances containing less water content, absorption is reduced accordingly. For example, mammal muscle is approximately 75% water. As such absorption in mammal muscle is expected to be reduced by 25% as compared to pure water. That is, the bleached absorption coefficient through muscle should be $\alpha_B=1.125$ cm$^{-1}$.

At a depth of L=5 cm, using the value for the bleached absorption coefficient, $\alpha_B=1.125$ cm$^{-1}$, we expect $T=\exp(-\alpha_B L)=\exp(-1.125*5)=\exp(-5.625)=0.0036$. This means that, assuming the pulse width is comparable to the 90 fs coherence time of water, more than a third of a percent of the THz radiation is transmitted. While the preceding analysis was performed at 210 THz, the system is expected to behave similarly at 0.8 THz.

The signal reflected from a specimen requires measuring the round-trip signal. With 0.36% one-way transmission, the square of that (1×10$^{-5}$) is the round-trip signal. Assuming an IED reflectivity ~10%, the exit signal should be ~10$^{-6}$ of the incident intensity. For example, for a 10$^{12}$ W/cm$^2$ signal, the exit transmission intensity would be ~10$^6$ W/cm$^2$.

The foregoing absorption calculation does not include the effects of scattering. The exponential scattering coefficient of animal tissue is between 0.05 cm$^{-1}$ and 2.13 cm$^{-1}$ for frequencies between 0.02 and 2 THz. The lower limit is negligible compared to the bleached absorption coefficient, but the upper limit is not. As a result, scattering may provide an unsaturable linear baseline loss (unless coherent scatter occurs). This might reduce the two-way transmission to as little as 10$^{-10}$ of the incident signal making transmission a more favorable method for detection.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed:

1. A system to detect a material, comprising:
   a pulse generator to generate a terahertz pulse to excite molecules in the material that induces coherent bleaching in the material so as to reduce absorption of the terahertz pulse as it propagates through the material;
   a detector to detect a signal having spectral components in the terahertz region emitted from the excitations; and
   a processor to perform statistical analysis and signal processing on the detected signal to reduce false positives and false negatives of detection.

2. The system of claim 1, wherein the pulse generator is a NIR laser wherein a pulse generated by the NIR laser impinges a nonlinear medium to induce a short polarization having the form of a laser-pulse envelope to generate the terahertz pulse.

3. The system of claim 1, wherein the temporal width of the pulse is shorter than or approximately the same as the medium dephasing time of the medium in which the pulse is traveling.

4. The system of claim 1, wherein the generated pulse has a duration of less than 100 fs.

5. The system of claim 3, wherein the generated pulse has a peak power greater than 1 TW/cm$^2$.

6. The system of claim 1, wherein the detector comprises a nanoantenna array that is configured as a phased array to increase the field-of-view and to maximize capture of the retro-reflected signal.

7. The system of claim 6, wherein the nanoantenna array comprises a plurality of antennas tuned to detected frequencies in the terahertz region.

8. The system of claim 6, wherein the nanoantennas comprise a MIM diode.

9. The system of claim 6, wherein the nanoantennas comprise a MIIM diode.

10. The system of claim 1 wherein the processor performs wavelet analysis on the acquired THz spectral data.

11. The system of claim 10 wherein the wavelet analysis comprises performing a wavelet transform of the acquired THz data to obtain a plurality of wavelet coefficients.

12. The system of claim 1 wherein the determining comprises performing a matched filter analysis to the acquired THz data.

13. The system of claim 1 wherein the determining comprises performing a model-based frequency analysis to the acquired THz data.

14. The system of claim 1 wherein the determining comprises processing the acquired THz data by a neural network.

15. A method for detecting a material, comprising:
generating a pulse to excite molecules in the material;
inducing coherent bleaching in the material so as to reduce absorption of the terahertz pulse as it propagates through the material;
detecting a signal having spectral components in the terahertz region emitted from the excitations; and
performing statistical analysis and signal processing on the detected signal to reduce false positives and false negatives of detection.

16. The method of claim 15, comprising generating the pulse with a NIR laser by impinging a pulse generated by the NIR laser on a nonlinear medium to induce a short polarization having the form of a laser-pulse envelope to generate the terahertz pulse.

17. The method of claim 15, comprising generating a pulse having a temporal width shorter than or approximately the same as the medium dephasing time of the medium in which the pulse is traveling.

18. The method of claim 15, comprising generating a pulse having a duration of less than 100 fs.

19. The method of claim 18, comprising generating a pulse having a peak power greater than 1 TW/cm$^2$.

20. The method of claim 15, comprising detecting the signal using a nanoantenna array that is configured as a phased array to increase the field-of-view and to maximize capture of the retro-reflected signal.

21. The method of claim 15, comprising detecting the signal using a nanoantenna array having a plurality of antennas tuned to detected frequencies in the terahertz region.

22. The method of claim 21, comprising detecting the signal using a nanoantenna array comprising a MIM diode.

23. The method of claim 21, comprising detecting the signal using a nanoantenna array comprising a MIIM diode.

24. A method for classifying THz spectral data as representing specific objects, the method comprising:
simulating security screening scenarios;
generating a terahertz pulse to interrogate the objects that induces coherent bleaching in the objects so as to reduce absorption of the terahertz pulse as it propagates through the objects;
collecting THz spectral data representative of the objects in response to the generated terahertz pulse;
extracting features from the magnetic data that distinguish respective objects; and
performing a pre-classification optimization method on the features.

25. The method of claim 24 wherein the performing comprises performing a wavelet analysis.

26. The method of claim 24 wherein the performing comprises performing a matched filter analysis.

27. The method of claim 24 wherein the performing comprises analyzing aspects of the features using fuzzy logic rules.

28. The method of claim 24 further comprising populating a classification database with unique aspects of the features.

* * * * *